United States Patent [19]

Brecher et al.

[11] Patent Number: 5,544,256
[45] Date of Patent: Aug. 6, 1996

[54] AUTOMATED DEFECT CLASSIFICATION SYSTEM

[75] Inventors: Virginia H. Brecher, West Cornwall, Conn.; Paul B.-L, Chou, Montvale, N.J.; Robert W. Hall, Jericho, Vt.; Debra M. Parisi, Carmel; Ravishankar Rao, White Plains, both of N.Y.; Stuart L. Riley, Colchester, Vt.; Martin C. Sturzenbecker, Carmel, N.Y.

[73] Assignee: International Business Machines Corporation, Armonk, N.Y.

[21] Appl. No.: 142,157

[22] Filed: Oct. 22, 1993

[51] Int. Cl.$^6$ .............................. G06K 9/00; G06K 9/62; G06G 7/00
[52] U.S. Cl. ..................... 382/149; 382/159; 395/900
[58] Field of Search .................... 382/8, 149, 155, 382/159; 395/900, 3; 348/126, 125

[56] References Cited

U.S. PATENT DOCUMENTS

| | | |
|---|---|---|
| T944,007 | 3/1976 | Booth, Jr. et al. |
| 4,253,768 | 3/1981 | Yaroshuk et al. ............ 356/431 |
| 4,432,641 | 2/1984 | Caprari et al. ............... 356/237 |
| 4,477,926 | 10/1984 | Linger et al. .................. 382/8 |
| 4,519,041 | 5/1985 | Fant et al. ..................... 382/22 |
| 4,587,617 | 5/1986 | Barker et al. ................. 364/507 |
| 4,801,869 | 1/1989 | Sprogis .......................... 371/22.5 |
| 4,876,455 | 10/1989 | Sanderson et al. ............ 258/560 |
| 4,969,198 | 11/1990 | Batchelder et al. ........... 382/8 |
| 4,988,202 | 1/1991 | Nayar et al. ................... 356/394 |
| 5,085,517 | 2/1992 | Chadwick et al. ............. 356/394 |
| 5,086,397 | 2/1992 | Schuster et al. ............... 364/468 |
| 5,129,009 | 7/1992 | Lebeau ........................... 382/8 |
| 5,131,755 | 7/1992 | Chadwick et al. ............. 356/394 |
| 5,159,547 | 10/1992 | Chand ............................. 364/157 |
| 5,179,634 | 1/1993 | Matsunaga et al. ........... 395/75 |
| 5,191,638 | 3/1993 | Wakami et al. ................ 395/51 |
| 5,208,898 | 5/1993 | Funabashi et al. ............ 395/50 |

FOREIGN PATENT DOCUMENTS

| | | | |
|---|---|---|---|
| 3714011 | 2/1988 | Germany ............... | H01L 21/70 |
| 59-192944 | 11/1984 | Japan .................... | H01L 21/308 |
| 63-086421 | 4/1988 | Japan .................... | H01L 41/22 |

OTHER PUBLICATIONS

Chou, Paul, et al., "Automatic defect classification for integrated circuits", IBM, Jan. 26, 1993, pp. 1–25.
Poechmueller, W. et al., "Automatic Classification of Solder Joint Images," p. II A–933 (no date).
Chou, Paul, B., "Automated classification of Defects in S/C Manufacturing", IBM Research, 1993.
Colom, L. A. et al., "Defect Data Analysis in Integrated Circuit Circuit Manufacturing", 1975, pp. 1059–1060.
"Auto–Defect Detection/Visual Defect Review Inspection System", 1989, pp. 306–307.
"Electronic Mask Verification", 1985, p. 845.
Lashgari, Bijan, "Fuzzy Classification with Applications to Geophysical Data", 1991, p. 309.
Wang, Fangju, "Fuzzy Expert System For Remote Sensing Image Analysis", 1943, pp. 848–851.
Yoda, Haruo, et al., "An Automatic Wafer Inspection System Using Pipelined Image Processing Techniques", 1988, pp. 4–16.
Cox, Earl, "Fuzzy Fundamentals", 1992, pp. 58–61.
Cox, Earl, "Adaptive Fuzzy Systems", 1993, pp. 27–31.

(List continued on next page.)

*Primary Examiner*—Jose L. Couso
*Assistant Examiner*—Matthew C. Bolla
*Attorney, Agent, or Firm*—Scully, Scott, Murphy & Presser

[57] ABSTRACT

An integrated visual defect detection and classification system. The invention includes adaptive defect detection and image labeling, defect feature measures, and a knowledge based inference shell/engine for classification based on fuzzy logic. The combination of these elements comprises a method and system for providing detection and analysis of product defects in many application domains, such as semiconductor and electronic packaging manufacturing.

52 Claims, 7 Drawing Sheets

OTHER PUBLICATIONS

Cox, Earl, "Fuzzy Logic Flowers in Japan", 1992, pp. 32–35.

Rao, A. Ravishankar, et al., "A Classification Scheme for Visual Defects Arising in Semiconductor Wafer Inspection", 1990, pp. 398–406.

Mandeville, Jon, R., "Novel Method for Analysis of Printed Circuit Images", 1985, pp. 73–86.

Keller, James M. "A Fuzzy K–Nearest Neighbor Algorithm", 1985, pp. 258–263.

Chang, Robin, L. P. et al., "Fuzzy Decision Tree Algorithms", 1977, pp. 264–270.

Nath, A. K. et al., "On the Design of a Classifier with Linguistic Variables as Inputs", 1983, pp. 241–257.

Zadeh, Lotfi A., "Outline of a New Approach to the Analysis of Complex Systems and Decision Processes", 1973, pp. 46–62.

Cho, Tai–Hoon et al., "A Neural Network Approach to Machine Vision Systems for Automated Industrial Inspection", 1991, pp. I–205–I210.

Keller, James M. et al., "Incorporating Fuzzy Membership Functions into the Perception Algorithm", 1985, pp. 468–474.

Ishibuchi, Hisao et al., "Pattern Classification by Distributed Representation of Fuzzy Rules", 1992, pp. 643–650.

Dralla, John R. et al., "Automatic Classification of Defects in Semiconductor Devices", 1990, pp. 173–182.

Polzleitner W. et al., "Real–Time Classification of Wooden Boards", 1990, pp. 38–49.

Cho, Tai–Hoon et al. "A Computer Vision System for Automated Grading of Rough Hardwood Lumber Using a Knowledge–Based Approach," 1990, pp. 345–350.

Koivo, A. J. et al., "Robust Image Modeling For Classification of Surface Defects on Wood Boards", 1989, pp. 1659–1666.

Tech, E. K. et al., "Automated Visual Inspection of Surface Mount PCBs", 1990, pp. 576–580.

Giet, Johannes, "Multiresolution Image Processing for Rough Defect Classification", 1990, pp. 214–224.

Dom Byron E., "The P300: A System for Automatic Patterned Wafer Inspection", 1988, pp. 205–221.

Ejiri, Masakazu et al., "Knowledge–Directed Inspection for Complex Multilayered Patterns", 1989, pp. 155–166.

Nafarieh, Asghar et al., "A Fuzzy Logic Rule–Based Automatic Target Recognizer", 1991, pp. 297–312.

ADE Corporation, Newton, Mass., Advertisement, "Semiconductor International", Jul. 1993. ADE undated product information sheets.

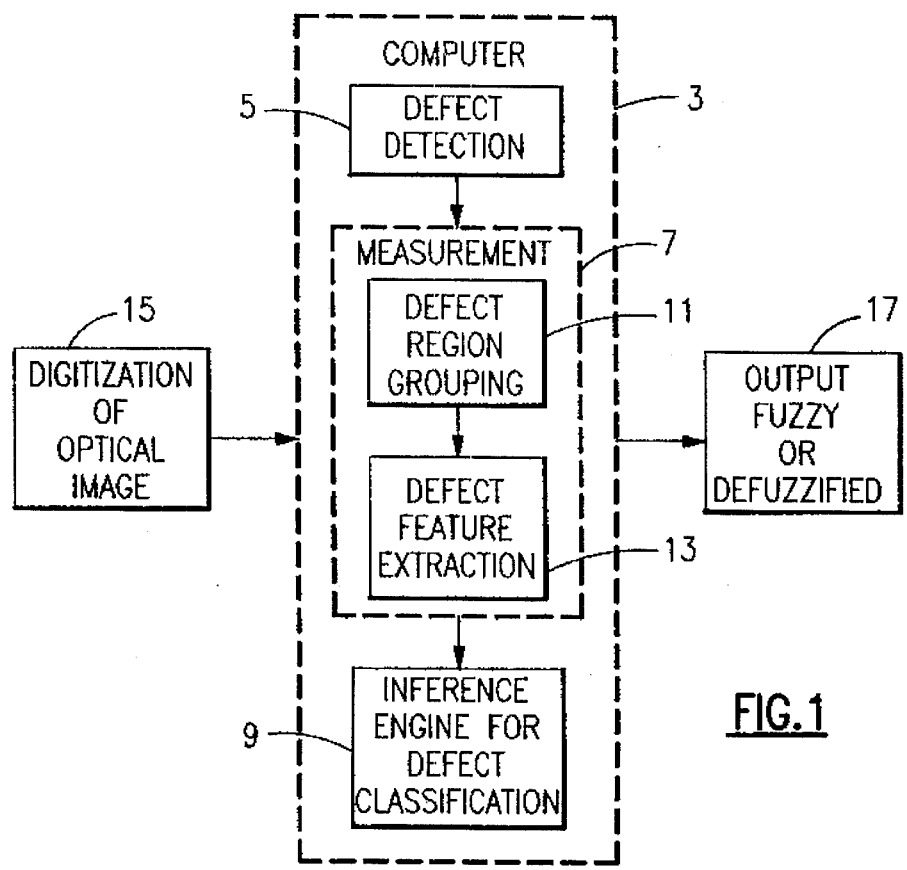
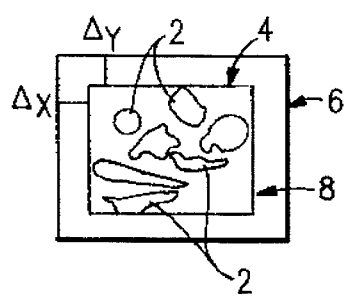
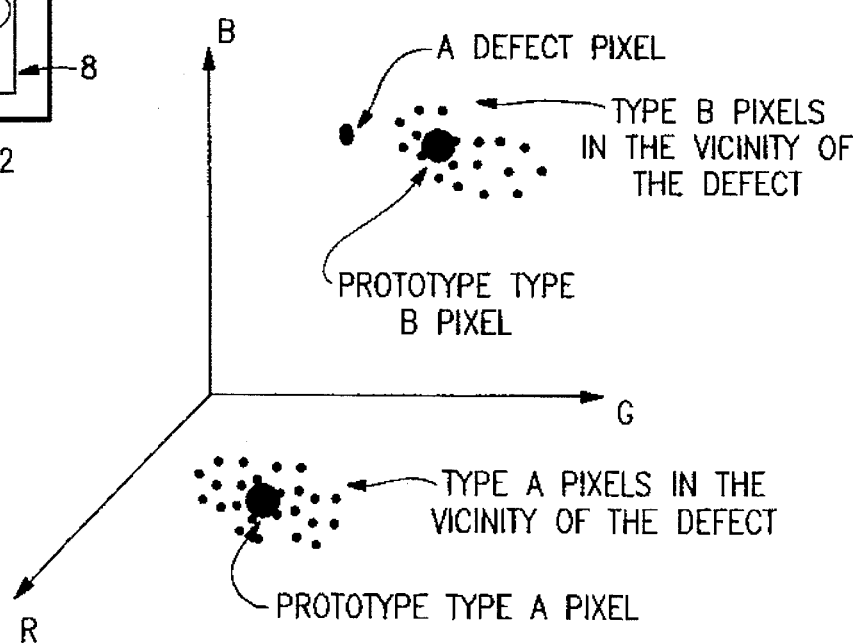

AUTOMATED DEFECT CLASSIFICATION SYSTEM

BACKGROUND OF THE INVENTION

1. Field of the Invention

This invention relates to a method and apparatus for defect detection and classification. More particularly, the invention relates to an automated defect classification system using fuzzy logic to automatically analyze measurements of various features of the defect and to automatically classify the defect based on the analysis.

2. Description of the Prior Art

Visual defect inspection and classification have become essential parts of many electronics manufacturing processes. Whale defect detection is critical for ensuring product quality, defect classification provides the information necessary to correct process or product problems. Defect classification is the task of sorting the defects into a set of predefined, meaningful categories often related to causes (e.g. foreign material) or the consequences (e.g. killer vs. cosmetic) of the defects. The classification data are commonly used in yield prediction, process diagnosis., and rework/scrap decisions.

Currently, many defect detection tools are available, each tailored for inspecting certain products with the objective of locating defects accurately while maximizing throughput. The output of these tools reveals little information about the defects themselves and hence is usually reviewed by human operators. In the defect review process, the operator first locates (redetects) the defect in the microscope field of view, then classifies the defect based on its appearance and context. This process is usually more time consuming than the initial detection. Hence it is customary to review and classify only a small sample of the detected defects. Moreover, operators tend to be inconsistent and defects are often misclassified. Accuracy rates as low as thirty to fifty percent are common in semiconductor manufacturing lines. Automating the classification process would reduce the operator work-load, allow more defects to be reviewed, and improve the accuracy of defect calls.

Many automated machine vision defect detection systems have been developed for manufacturing inspection and a few of these systems include defect classification capability. Although the reference comparison method generally used to detect defects is applicable to a wide variety of products, defect classification, when it is included in the automated inspection system, is limited in application to the target product. That is, the machine vision based classification is based on product specific parameters and cannot be ported from one application to another.

In cases such as sheet metal, paper and textile manufacture, the product is statistically homogeneous, so that anomalies can easily be segmented and sorted on the basis of size, shape, brightness and/or color. Examples of automatic defect classification in these industries can be found in U.S. Pat. No. 4,519,041 directed to real time automatic surface imperfection detection and classification; Cho, et al., "A computer vision system for automated grading of rough hardwood lumber using a knowledge based approach," International Conference on Systems, Man and Cybernetics, pp. 345–350, IEEE, 1990; Cho et al., "A neural network approach to machine vision systems for automated industrial inspection," International Joint Conference on Neural Networks, pp. 205–210, IEEE, 1991; and Giet et al., "Multi-resolution image processing for rough defect classification," in Industrial Inspection II, pp. 214–224, SPIE, 1990. In the electronics industry, defect classification has been generally limited to printed circuit board inspection. Current implementations can sort defects into broad categories such as shorts, opens, pinholes and extraneous material. This can be accomplished by performing design rule checks on the simple (binary) pattern as shown by Mandeville, "Novel method for analysis of printed circuit images," IBM Journal of Research and Development, no. 1, pp. 73–86, 1985. Recently, systems have been developed to detect and classify defects on populated printed circuit boards, an example of which is described in Teoh, et al., "Automated visual inspection of surface mount pcb's," in 16th Annual Conference of IEEE Industrial Electronics Society, pp. 576–580, IEEE, 1990. Defect classification for mask inspection is disclosed in U.S. Pat. No. 4,587,617, directed to image inspection system for IC wafers. Only a few attempts to classify defects on integrated circuits have appeared in the literature. They are similar to printed circuit board inspection systems and limited to defects on wiring levels, Dralla et al., "Automatic classification of defects in semiconductor devices," Integrated Circuit Metrology, Inspection and Process Control IV, pp. 173–182, SPIE, 1990, or simple rectilinear patterns, Chi, et al., "Using the cesm shell to classify wafer defects from visual data," in Automated Inspection and High Speed Vision Architectures III, vol. 1197, pp. 66–77, SPIE, 1989. An exception is Rao et al., "A classification scheme for visual defects arising in semiconductor wafer inspection," Journal of Crystal Growth, vol. 103, no. 1–4, pp. 398–406, 1990, which classifies texture anomalies on silicon.

Despite these attempts at automatic defect classification, most inspection systems rely on manual review of defects. Since many defects will be unique to certain products and to certain stages in the product's manufacture, it would be very costly to develop specific defect classification systems for each inspection. Furthermore, inspection requirements are greatest in the early stages of product development. This means that classification tools must be developed rapidly, a requirement that adds to their cost and limits their flexibility.

Traditional approaches to classification fall mainly into two categories: rule-driven (top-down) and data-driven (bottom up). The rule-driven approach seeks to incorporate expert knowledge. It is most often implemented in the form of a decision tree using binary ('deterministic') logic. This has the effect of drawing rigid boundaries around classes in the feature space. For example, a defect with an area of X units might be considered gross, while a defect with an area X-1 units might be called not-gross. This approach fails to capture the uncertainty and imprecision which is characteristic of the term "gross defect". Another problem with the decision tree is that it encodes knowledge in a highly structured form. There is no provision for processing of conflicting rules, which may represent disagreement among experts. These weaknesses of the traditional AI approach often lead to adoption of the data-driven approach. A data-driven approach abandons the attempt to directly encode expert knowledge and relies instead on "learning" how to classify based on a corpus of already classified training data. There are three general methods that are widely used: discriminant algorithms, multilayer neural networks, and Bayesian theory.

Examples of algorithmic techniques include nearest-neighbor and linear discriminant (perceptron) methods. In each case, the algorithm is in essence a strategy for drawing rigid class boundaries in feature spaced based on the training data. Again, there is no notion of uncertainty built into these methods. Neural networks estimate class boundaries using stochastic approximation in the context of a computational architecture derived from neural biology. In principle, given enough data, the right arrangement of neurons, and enough time to converge to a solution, neural networks can learn even very complex, non-linear class boundaries. However, there are numerous practical problems with neural nets including availability of adequate training data and deciding on the correct architecture to use. Neural networks are also difficult to tune except by complete retraining. So far, they seem best suited to simple two-way classification or decision problems (e.g. is this object a bomb or not?).

The only method mentioned so far which incorporates uncertainty in a fundamental way is Bayesian theory. Rather than drawing class boundaries in feature space, Bayesian classifiers estimate probability distributions for various events as a function of feature vectors. This combined with a priori probabilities of occurrence of each type of event yields a net probability for each event given an input feature vector. The Bayesian classifier can then choose the event with highest probability (thus, Bayesian classifiers are said to minimize the overall probability of classification error), or can simply report the calculated probabilities to the user.

Bayesian classifiers have proven successful in a number of applications. However, they typically rely on an explicit mathematical model for probability distributions, for example, normal (Gaussian) or logistic distribution functions. If the data does not fit the chosen model well, this approach is less effective. Also, while this approach captures uncertainty in the modeling of event arrivals as random variables, it does not deal with imprecision in the definition of classes. Thus, Bayesian theory is more difficult to apply in situations where class definitions are vague and non-exclusive (an event may legitimately belong to more than one class).

Yoda et al. describe a wafer defect detection and classification system in "An Automated Wafer Inspection System Using Pipelined Image Processing Techniques," IEEE Transactions and Pattern Analysis and Machine Intelligence, Vol. 10, No. 1, Jan. 1988. The classification part of the system takes the defect image and compares it to binary images representing each design level of the product. The features are collected from projecting the defect area on to each pattern level and computing the shape of the defect that resides on that level's pattern. The specific features are area and bounding box. These features are channeled into a simple rule based classifier that does not provide for uncertainty in the defect measures.

There is a broad literature on using concepts of fuzziness as an uncertainty measure in classification applications. Much of this literature, however, deals with the incorporation of fuzziness into data-driven discriminant algorithms, such as fuzzy k-NN (k-nearest neighbor) algorithms. Keller, et al., "A fuzzy k-nearest neighbor algorithm," IEEE Transactions on Systems, Man and Cybernetics, vol. 15, no. 4, pp. 580–585, 1985. Such methods may perform somewhat better than discriminant algorithms which do not use fuzziness, but they retain most of the disadvantages of their non-fuzzy counterparts: they are totally dependent on the quality of their training data and they do not represent class vagueness in any realistic way. Fuzzy logic can also be used in a rule-driven fashion to encode expert knowledge. An early example of this in classification was the fuzzy decision tree, Chang et al., "Fuzzy decision tree algorithms," IEEE Transactions on Systems, Man and Cybernetics, vol. 7, no. 1, pp. 28–35, 1977. Again, fuzzy decision trees are an improvement over the bivalent type, but retain the disadvantage of being too dependent on hierarchical structure. While some human reasoning is structured in this way, much of it is not.

Fuzzy inference architecture has been used in control problems and other types of decision support applications, for example risk analysis or evaluation of candidates for a job. Wang, "A Fuzzy Expert System for Remote Sensing Image Analysis," Digest International Geoscience and Remote Sensing Symposium, Vol. 2, pp. 848–851, 1989, discloses the use of fuzzy logic for remote sensing of geographical images.

In spite of the importance of automating classification, to date there are no systems available that could meet defect classification requirements in the semiconductor manufacturing area. The failure to develop automated classification is primarily due to the problems of characterizing defects in conventional machine vision systems. The problems arise from the unpredictable appearance of defects, their size range (varying from below the optical resolution limit to very large), the difficulty of determining the three dimensional characteristics of a defect from a two dimensional image, and the large amount of acceptable process variation in the manufacturing process which can easily lead to false defect classifications. Current defect detection systems lack the resolution to perform classification. A truly generic defect classification system which can be quickly tailored to a new application would offer a great advantage over the current application of specific solutions. The present invention provides such a system.

SUMMARY OF THE INVENTION

The present invention is directed to an automatic defect classification system that comprises means for detecting object defects in a digital input image of an object, means for measuring a plurality of features of the object defects from the digital input image resulting in the formation of a plurality of defect feature measurements. A fuzzy logic inference engine is utilized to classify the object defects by applying if-then rules to fuzzy logic parameters derived from the plurality of defect feature measurements. The system and method of the present invention may be utilized to classify defects in a variety of products and it has been implemented in a defect classification system for semiconductor patterned wafers. In accordance with the method of the present invention, the defects are automatically classified by detecting the defects in a digital input image of an object, measuring a plurality of features of the object defects to form a plurality of defect feature measurements and classifying the object defects by applying a plurality of if-then rules to fuzzy logic parameters derived from the plurality of defect feature measurements.

The digital input image is typically obtained from an optical image of the object. In a patterned semiconductor wafer environment, optical defect detection tools are available and such tools may provide the optical image to be digitized by the system of the present invention. The defect detection in accordance with the present invention includes the formation of a label image that identifies the elements of the object in the optical scene. Defect pixels are adaptively labeled utilizing label distributions derived from non-defect pixels.

In order to obtain the feature measurements, defect pixels are grouped by first grouping connected defect pixels into defect regions and then grouping the defect regions into defect clusters based on one or more region grouping criteria. Defect feature measurements are then made from the defect clusters. For example, the feature can include size, shape, texture, location, composition, color and contrast in the semiconductor wafer implementation of the invention.

The fuzzy logic inference engine includes means for storing one or more feature fuzzy sets for each of the plurality of defect feature measurements and means for storing the plurality of if-then class rules which have an output class derived from one or more of the feature fuzzy sets. The system includes means for converting the defect feature measurements into fuzzy logic parameters and for comparing the fuzzy logic parameters with each feature fuzzy set of each class rule to produce a degree of match for each feature fuzzy set for each class rule. This system also includes means for combining the degree of match for each fuzzy set of each class rule to produce a degree of match for each class rule and means for combining the degree of match for each class rule to produce a defect class fuzzy set for each object defect. The system also includes means for defuzzifying the defect class fuzzy set to thereby classify the object defect as one of the plurality of defect classes.

BRIEF DESCRIPTION OF THE DRAWINGS

FIG. 1 is a block diagram of the automatic defect classification system of the present invention.

FIG. 2 is a representation of a defect cluster in the method of building a label distribution.

FIG. 3 is an RGB color space representation of pixels in the vicinity of a defect pixel.

DETAILED DESCRIPTION OF THE INVENTION

Figure 5:
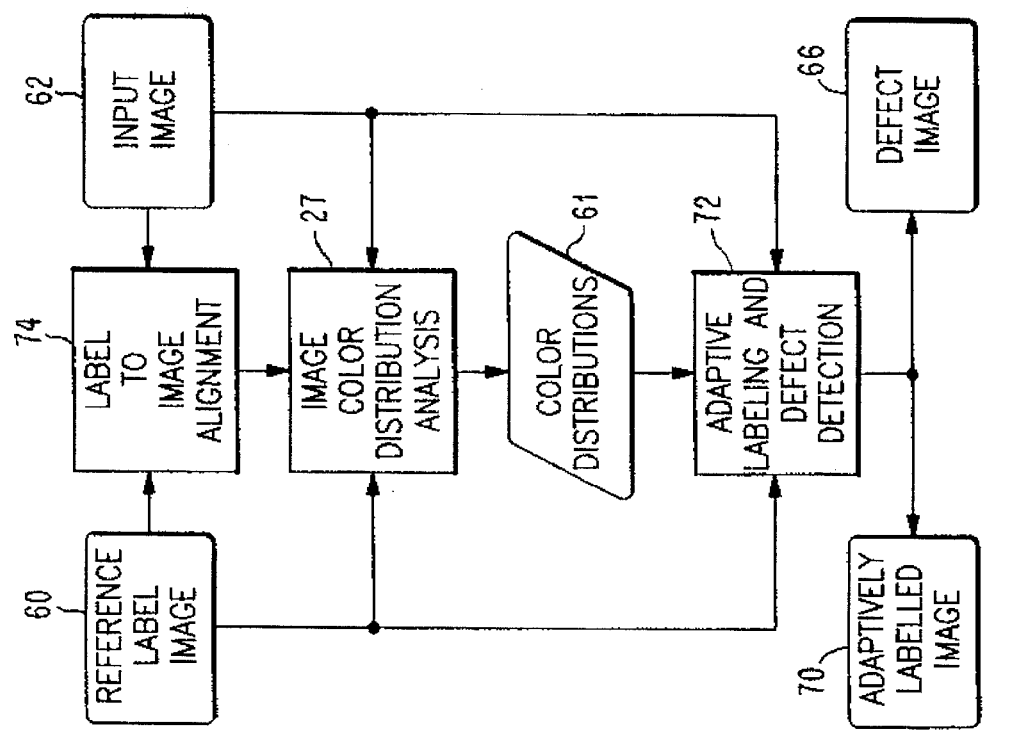
FIGS. 5 and 6 are block diagrams of alternative embodiments of the system and method for forming adaptively labeled images.

The present invention is directed to an integrated defect detection and classification methodology and system. The method of the present invention has been implemented as an automated defect classification system for semiconductor array products. The present invention offers a robust, flexible, easy-to-use, and cost-effective method and system for customizing defect detection and classification solutions to various industries and products. The basic elements of the invention consist of adaptive defect detection, image labeling, defect feature measures, and a knowledge based inference shell/engine for classification based on fuzzy logic. These elements are combined in order to provide easy-to-use, expandability, and low system development and maintenance costs. The present invention provides an effective solution to the prior art problems of defect detection and classification in a manufacturing environment.

The defect classification system of the present invention consists four subsystems of: defect detection, defect feature measurement which includes region grouping, and feature extraction, and defect classification. FIG. 1 illustrates the four subsystems of the invention. As shown in FIG. 1, the system is implemented in a computer 3 having means 5 for detecting object defects in a digital input image of an object, means 7 for measuring a plurality of features of the object defects from the digital input image to form a plurality of defect feature measurements, and fuzzy logic inference engine means 9 for classifying the object defects by applying a plurality of if-then rules to fuzzy logic parameters derived from the plurality of defect feature measurements. The defect measurement means includes means 11 for defect region grouping and means 13 for feature extraction.

The system of FIG. 1 further includes means 15 for forming a digital input image from an optical image of the object. The system output 17 can output the classification data in fuzzy form or defuzzified form which can depend on the nature of the results or user choice.

Each sub-system corresponds to a software module, with well-defined interfaces between the interacting modules. The functions of each module in terms of the inputs and outputs and the mechanisms to accomplish the functions will be described below.

The following terms are defined as used herein:

Image: A two dimensional array which is a spatial representation of a scene.

Pixel: Each array element of the image is called a pixel. A pixel represents a measurement or property at a given position in the scene.

Input Image: An image in which the pixels represent the camera measurements of the object's color and/or brightness.

Label Image: An image in which each pixel is assigned a symbolic label which identifies the objects in the scene. Typically in constrained environments, the labels are predefined, mutually exclusive and exhaustive.

Image labeling: The process of assigning labels to pixels.

Defect Image: An image in which pixels are labeled as "defective" or "non-defective".

Adaptive Distribution for label L: A probability distribution of some image measure estimated by sampling input image pixels labeled as L. The image measure for instance could be of gray level, color, or spatial neighborhood statistics. The probability distribution is typically modeled as a Gaussian.

Reference Label Image: A label image of which the pixel labels represent the reference object identities in the scene.

Adaptively Labeled Image: A label image derived by labeling the Input Image using the Adaptive Distributions for all the labels L in the Reference Label Image.

Most of the existing optical defect detection tools in the electronics manufacturing industry and many in other industries are based on an image-to-reference comparison scheme whereby a digitized product image is compared to some kind of reference data to detect abnormalities. Typically, the output of these tools is a binary image where each defect pixel is coded as a "one" and each good pixel as a "zero". This invention carries the process several steps further by computing (1) a conventional binary defect image, (2) a reference label image, (3) label distributions and (4) an adaptively labeled image for the area under inspection. The label is a code denoting which part of the product is represented by a pixel. In integrated circuit inspection applications, the label typically represents a material or structure, such as nitride or trench. The adaptively labeled image is derived using the image measurement distributions of the area under inspection, making the labeling insensitive to acceptable variations in brightness, color and texture of the product surface. By providing label as well as defect data, the invention is able to provide a richer and more flexible set of features on which to base classification.

Initially, the adaptive labeling procedure for labeling the input image when a reference label image is available is described. With minor modifications, the procedure is also used in the case when the reference label image must be computed dynamically. Adaptive image measurement distributions are computed by sampling the non-defect pixels in the input image with respect to each label indicated in the reference label image. The adaptively labeled image is the reference label image with labels of the pixels identified as defects replaced by labels computed using the input pixel values and the adaptive image measurement distributions. More precisely, adaptive image labeling is the process of re-labeling the defect pixels by using the adaptive image measurement distributions. This process involves the identification of that distribution to which the defect pixel is most likely to belong. For instance, this identification can be done through Maximum Likelihood Estimation (MLE). Thus, one can decide if a defect pixel resembles any of the ideal labels in the label image through a suitably defined similarity or likelihood measure. For instance, does the defect pixel look more like a metal or more like polyimide? If the likelihoods are low for all labels distributions, an unknown label is used for such pixels, indicating that the defect may be caused by events not modeled by the set of labels.

In adaptive labeling statistics are gathered locally around the defect region. This innovation enables the algorithm to adapt to changing illumination levels, shading, and part-to-part variations.

As an example, the use of a color distribution to perform adaptive labeling is described. First, non-defect pixels are sampled in the vicinity Of the defect. This enables the system to build the color distribution for each of the L labels in the Label Image. The sampling can be done as indicated in FIG. 2, in which a cluster of defects 2 are enclosed in a bounding box 4. The bounding box 4 for the defect cluster is augmented by $\Delta_x$ and $\Delta_y$ to yield the augmented bounding box 6. Statistics are gathered from the non-defect pixels in the area 8 between the two bounding boxes.

One way of characterizing the distribution for the $i^{th}$ Label Image is through the mean vector $M_i$ and the covariance matrix $\Sigma_i$ in rgb color space. The covariance matrix captures the second order moments of the distribution of the non-defect pixels in rgb color space. Thus M is a vector with three components, the mean red, green and blue values, and $\Sigma$ is a 3×3 matrix. FIG. 3 shows an rgb color space representation of the vicinity of the defect region. Two types of materials, type A and type B are depicted. The pixels representing types A and B form two clusters, represented by data close to each other. The average of each cluster denotes the prototype pixel for that cluster.

Given a defect pixel, we can then determine whether it belongs to any one of the distributions of the L labels in the Label Image. Let the defect pixel have rgb values represented by a vector X. One possible way of doing this is to calculate its distance $D_i$ (which is known as the Mahalanobis distance) from each of the prototype reference label pixels $M_i$ found above as follows:

$$D_i = (X - M_i)\Sigma_i^{-1}(X - M_i)^T$$

If the minimum distance, $\min(D_i)$ is less than a threshold T, we relabel the defect pixel to be of the $i^{th}$ class. Otherwise, the defect pixel is relabeled as unknown.

Reference images are required for defect detection and for adaptive labeling. This invention includes methods designed for exploiting three different types of reference data: reference images created off-line, reference images derived from other product areas of identical pattern, and reference images generated from design data.

Figure 4:
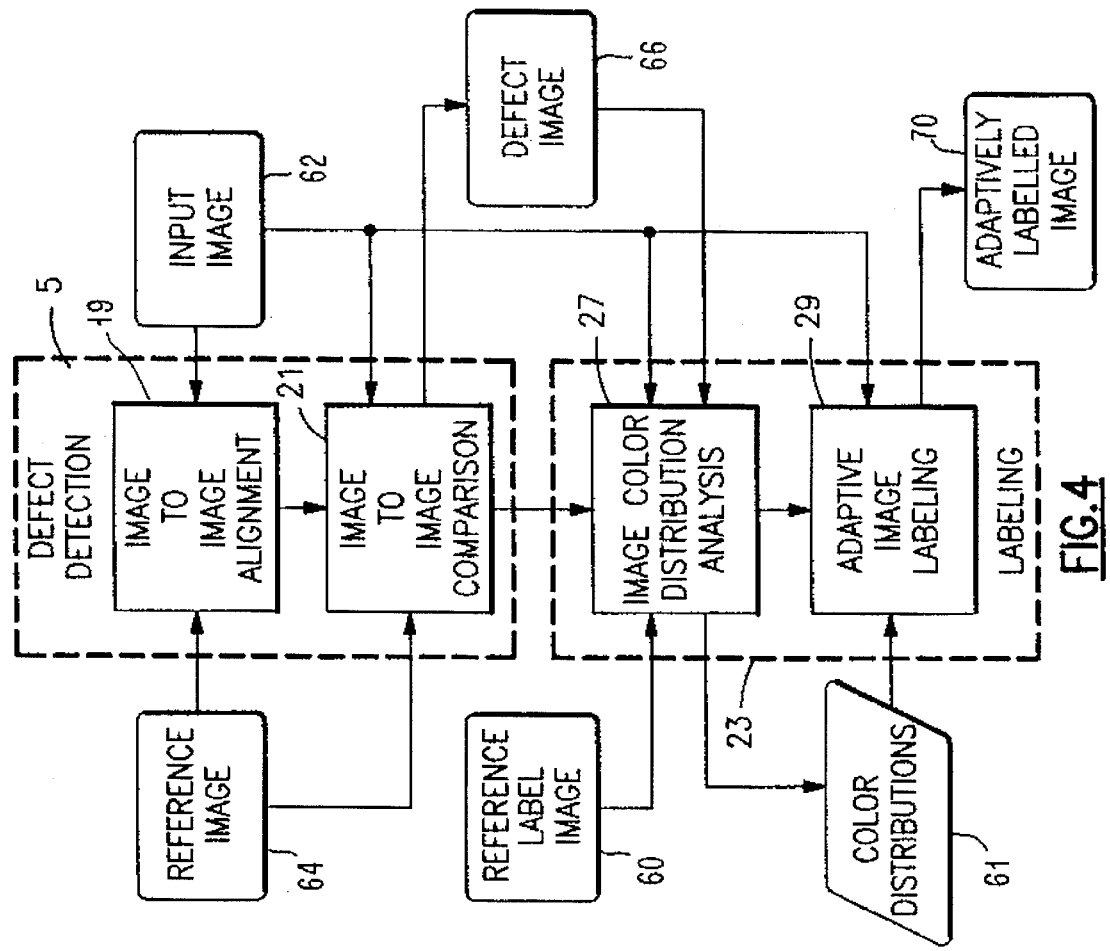
FIG. 4 is a block diagram of one embodiment of the system and method for forming an adaptively labeled image.

For creating reference images off-line, statistical data are collected for each pixel by using a large sample of images of defect-free parts. One possible statistical representation of a set of defect-free images is a mean image and a standard deviation image. Statistical testing is performed on each pixel in the input image to detect abnormalities. For instance, if a pixel value is more than three standard deviations from the mean, it is signaled as a defect. The reference label image is created manually or semi-automatically by labeling the mean image. FIG. 4 is a representation of the defect detection subsystem when the reference label image 60 is created offline. The defect detection means 5 includes means 19 that aligns the input image 62 to the reference image 64 by finding their maximum correlation coefficient, and means 21 that compares the input image 62 to the reference image 64 and produces a defect image 66. Labeling means 23 includes means 27 that computes the image measurement distributions, for example color distributions 61, based on the reference label image 60 and the input image 62, along with the defect image 66. Adaptive image labeling means 29 outputs an adaptively labeled image 70.

Reference images can also be generated from design data. In many domains, product design data in terms of pattern geometry and materials are available, and reference label images can be created from such data using rasterization procedures. As shown in FIG. 5, the purpose here is to utilize the reference label image 60 to create via image color distribution analysis means 27 the adaptive image measurement distributions, such as color distributions 61, for detecting defects and adaptively labeling the input image 62. The color distributions 61 are input to adaptive labeling and defect detection means 72 which outputs adaptively labeled image 70 and defect image 66. The key is to achieve fast and robust alignment between the input image 62 and the reference label image 60 via label to image alignment means 74. The following method is illustrated in FIG. 5: for each possible alignment location, consider the image measurements of the pixels for each (presumed) label to form a cluster in the measurement space, and compute the ratio of the inter and intra-cluster distances (with some suitable metrics) of the clusters. At an alignment location, if the labels describe the image well (well aligned), the pixel measurements of a particular label would be similar and tend to cluster together in the image measurement (e.g. rgb color) space. If the labels describe the image poorly (misalignment), then the pixel measurements of a (presumed) label would spread widely in the measurement space. The ratio of inter-cluster distance to intra-cluster distance is a measure of the goodness of an alignment, and one possible way of defining this is $$\rho = \frac{\sum_{i=1}^{i=N} \sum_{j,k \in C_i, j \neq k} d(I_j, I_k)}{\sum_{m=1,n=1}^{m=N, n=N} d(\bar{IC}_m, \bar{IC}_n)}$$

where N is the number of clusters, $C_i$ denotes the $i^{th}$ cluster, $xC_m$ denotes the centroid of the $m^{th}$ cluster, and d() denotes a suitable distance metric (e.g. Euclidean distance). $\rho$ is minimized at the best alignment location, and is typically a smooth function near the optimal location. Thus, gradient search schemes can be used to speed the alignment process.

Figure 6:
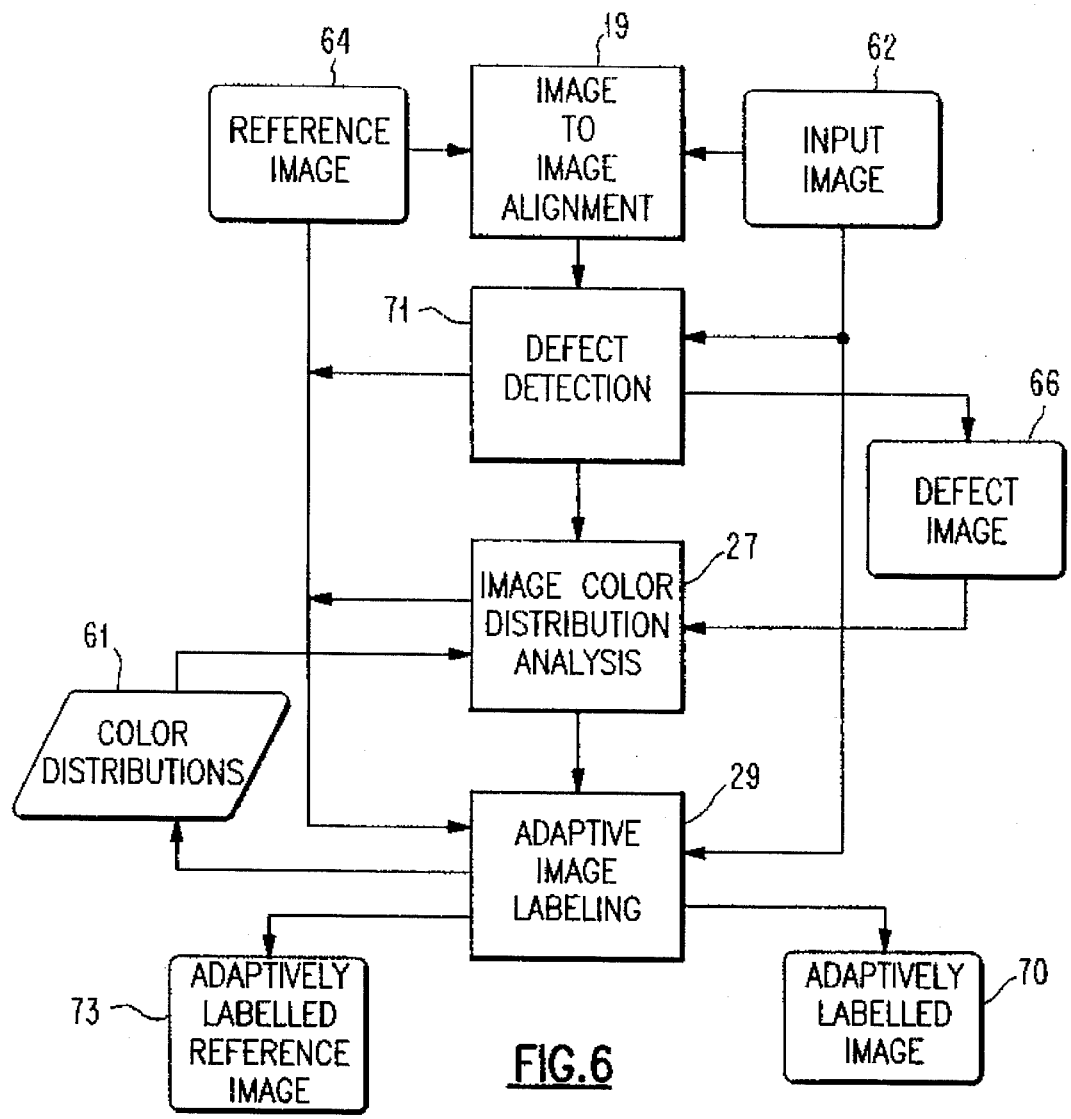

Reference images may also be derived from other product areas. In this method, the product area under inspection is compared with other product areas known to be of the same pattern. Typically, a reference image 64 is derived from one or more images of identical pattern as the basis for comparison. In this case, the reference label image is usually unavailable and must be computed dynamically using the reference image 64. FIG. 6 illustrates this process. Alignment means 19 aligns the input image 62 and reference image 64 and outputs the results to defect detection means 71. Means 71 create defect image 66. The defect detection means 71, defect image 66 and color distributions 61 are analyzed by means 27 and output to labeling means 29 which outputs adaptively labeled reference image 73 and adaptively labeled image 70. Since the labels involved in the product are known a priori, a number of automated labeling schemes can be used for such purpose. The same MLE procedure described above for creating dynamically labeled images can be used for creating the reference label image except that the pre-defined set of labels is exhaustive, resulting in no need for the unknown label.

Figure 8:
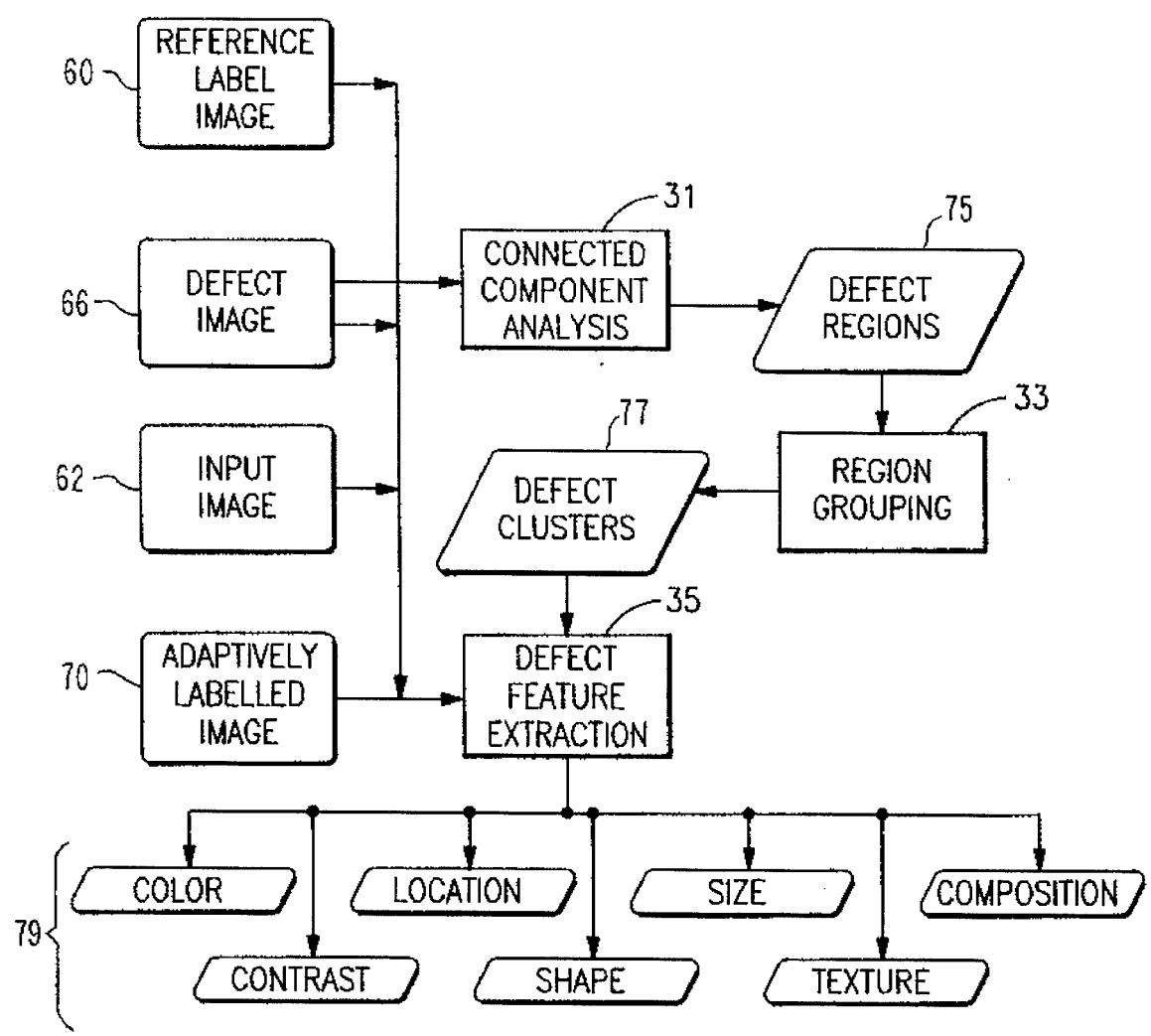
FIG. 8 is a block diagram of the system and method of the present invention for grouping of defects and feature measurement and extraction.

The defect image computed by the detection process is a binary image 66, with 1 indicating defect and 0 otherwise. It is difficult to make inferences using pixel-based defect representations directly since the information at this level is too sparse to handle. The present invention uses the defect grouping and defect feature measurement processes to extract condensed, relevant information from the pixel representation. The system for defect feature measurement is shown in FIG. 8.

Two tiers of grouping are performed after defect detection. First, in means 31, connected defect pixels from defect image 66 are grouped into isolated regions, thus transferring the pixel-based defect representation into a region-based description consisting of the coordinates of the region interior and/or border pixels and basic region measurements such as location, area, perimeter and shape of the region. Thus, means 31 measures and stores the defect region measurement data 75. Second, in means 33, such regions are grouped into region clusters 77 based on grouping criteria with each cluster corresponding to a defect in the scene. This level of grouping is needed because a single defect observed on the product may manifest itself as multiple defect regions. This occurs due to the following reasons: typically the defect detection process tends to be less sensitive around the object boundaries in order to reduce false calls. A spatially connected defect tends to get fragmented into multiple regions by the detection process, and the original defect may consist of spatially disjoint regions as in the case of a scratch.

Figure 7:
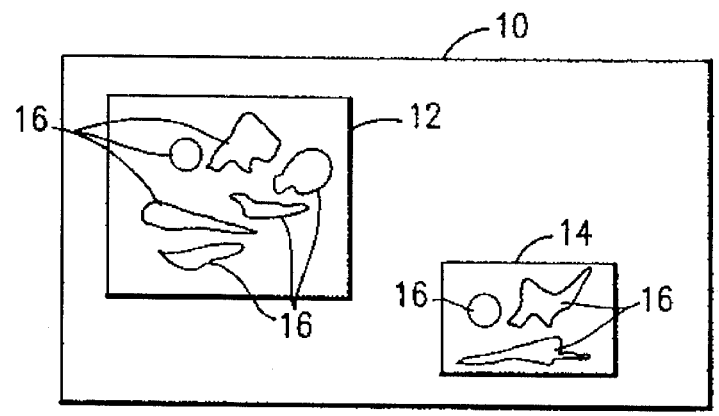
FIG. 7 is a representation of an object scene showing two defect clusters.

FIG. 7 shows a scene 10 with two defect clusters 12 and 14 each consisting of a set of defect regions 16 grouped together based on a grouping criteria. Two examples of grouping criteria that can be used to group regions into a cluster are the spatial proximity criteria and the common feature criteria. The spatial proximity criteria are designed to group nearby regions together, eliminating the fragmentation problem caused by the detection process. The spatial proximity process is illustrated in FIG. 7. For example, defect region can be grouped into one cluster as long as the distance between their bounding boxes is less then a predetermined number of pixels that can be set by the user.

The common feature criteria groups regions that possess some common or similar feature values, measured in the pixel grouping step. For example, regions (centroids) lying on a line are grouped together since they might be caused by a scratch and regions of similar colors are grouped together since they might be the result of the same chemical contamination. Region grouping is carried out using the well-known union-find algorithm. First, each region is considered as the root of a tree. Thus, we have as many trees as the number of regions initially. Then the regions are compared pairwise for similarities using the grouping criteria. Similar regions are united to form larger trees. Each of the resulting trees corresponds to a cluster. It is possible to have multiple clusters or defects in one field of view. This-defect-based representation allows a separate treatment for each defect. Means 33 thus, measures and stores defect cluster measurement data 77.

After the defect cluster measurements are obtained, means 35 measures a set of defect features 79 based on the classification criteria of a given application using the outputs 60, 66, 62 and 70 from the detection process.

Different applications may use different sets of defect features to maximize the classification accuracy and to minimize the computation load. The user can choose the set of suitable measurements according to the defect classification needs. The defect features for wafer pattern defect detection and classification may be broken down into the following categories: size, shape, texture, location, composition, color and contrast.

Since we classify an entire defect cluster, and not individual defect regions, our measurements must be reported at the cluster level. There are two ways of doing this:

1. Compute measurements for each region, and then aggregate these over the whole cluster.

Figure 9:
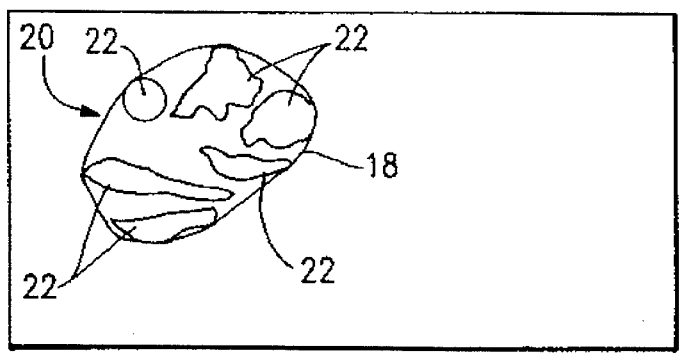
FIG. 9 is a representation of a convex hull of a defect cluster for obtaining defect measurements.

2. Calculate a bounding curve for the set of all regions in the cluster, and measure properties with respect to this bounding curve. For instance, as shown in FIG. 9, the convex hull 18 of defect cluster 20 can be calculated, and properties of the convex hull, such as its area and perimeter can be measured.

The present invention includes several features computed by using the adaptive and/or reference label images and the image measurement distributions provided by the defect detection process. The idea is to exploit as much as possible the static (e.g. the reference images) as well as the dynamic (e.g. statistics of the input image) information. The static information encodes how the product should be, and the dynamic information captures the process variations common to many manufacturing processes. Fusing such information enables the identification of salient features of the defects while remaining insensitive to minor process variations.

For example, for the size feature, we provide the maximum, the minimum, the average, and the sum of the region areas 22 in the cluster 20 as well as the area of its convex hull 18.

Typical measurements for shape include circularity and eccentricity. Shape is an important feature as certain defects can be distinguished based on whether they are round or elongated. Several shape measures are used. Circularity of a region is defined as $$\text{Circularity} = \frac{\text{Perimeter}^2}{4\pi\,\text{Area}}$$

The perimeter of a region is the sum of Euclidean distances between successive boundary points. Note that the perimeter of a digital straight line is zero.

The average circularity of all the regions within a cluster as well as the maximum circularity are measured. In addition, the circularity and perimeter of the convex hull are also measured. For a given area, the most compact shape is a circle. In other words, a circle minimizes the perimeter for a given area. Thus, the circularity for a perfect circle is 1, and as the shape becomes more elongated, the circularity measure increases.

Figure 12:
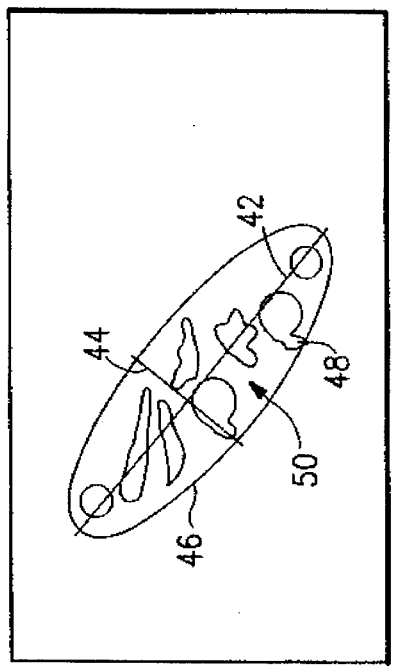
FIG. 12 is a representation of a defect cluster and the measurement of the minor and major axis to determine the shape of the cluster.
Figure 13:
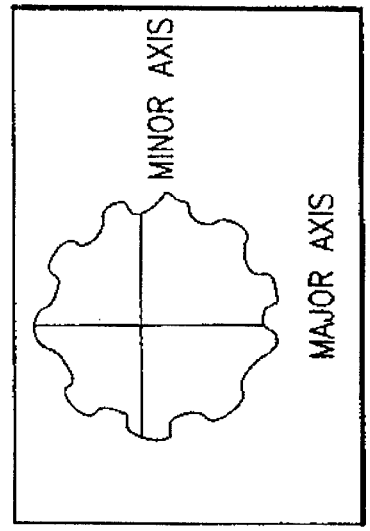
FIG. 13 is a representation of shape of a defect cluster having an eccentricity close to one but a circularity much higher than 1.

Eccentricity is a moment-based shape feature. As shown in FIG. 12, it can be measured as the ratio of the major axis 42 to minor axis 44 of the bounding ellipse 46 around defect region 48 within cluster 50. Eccentricity is similar to circularity, but can be considered a "smoother" measure of shape in the following sense. Consider a cogged wheel as shown in FIG. 13. Its circularity will have a high value (as its perimeter can be made very large). However, its eccentricity will stay close to 1, as the axes of the bounding ellipse remain constant. Thus, the circularity measure for this shape is influenced by the long, jagged perimeter.

The composition feature measures what the defect is composed of with respect to the Label Image. Using this feature in the semiconductor wafer application, the percentage of the defect that is extra metal in the polyimide area or vice versa can be measured. With such measurements, it is easy to detect intrusions, extensions, and shorts for circuit inspection. Sometimes defects can be caused by missing or displaced patterns. For instance, an entire trench could be missing. One would then like to know whether the defect region is composed of pixels that resemble the background nitride. Such a decision is made possible by the composition measures.

The composition measures are computed by using the adaptive labeling process described above. First, non-defect pixels are sampled in the vicinity of the defect and prototypes for each of the label classes are built. For instance, we can find the (r,g,b) values for the prototype trench and nitride pixels in the vicinity of the defect as shown and described with respect to FIG. 2.

Figure 14:
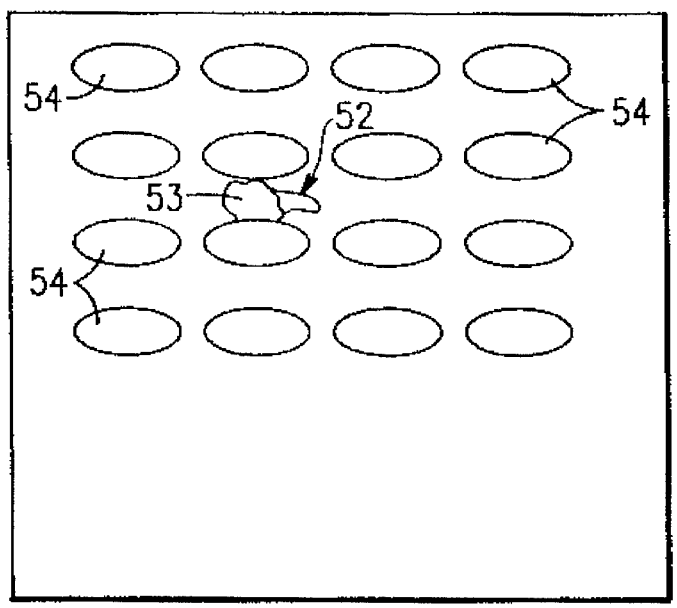
FIG. 14 is a representation of the semiconductor wafer having trench and nitride regions showing a defect acting as a short between two trenches.

Given a defect pixel, a determination can be made whether it matches any of the above prototypes. This match is based on a nearest distance technique, and is illustrated in FIG. 3. Therefore, it can be determined whether a defect pixel belongs to any one of the distributions of the L labels in the Label Image. Thus, it can be determined whether a defect pixel looks like trench, nitride or is totally unknown. FIG. 14 illustrates the principle and shows how the information can be used to decide shorts. The defect region 52 is composed of a portion 53 that has the same appearance as trench regions 54. Since the defect 52 touches two trenches 54, this would be called a short.

Composition measures are determined as follows: suppose a defect lies on two reference labels, label 1 and label 2. Further, let $N_2$ be the number of defect pixels on label 1, and $N_2$ the number of defect pixels on label 2. After the adaptive labeling process, we end up with $M_2$ pixels of type 2 on label 1 and $M_1$ type pixels on label 2. Then the term "composition 1 on 2" refers to $$\text{Composition AonB} = M_1/N_2$$

The composition of true defect on 1 or 2 can be determined in the same manner.

Suppose a high value (close to 100%) for "composition trench on nitride" is obtained (i.e. composition 1 on 2). This means that the defect pixels that fall on the nitride region are actually formed of trench material. Similarly, a high value for "composition nitride on trench" (i.e. composition 2 on 1) means that the defect pixels that fall on the trench region are actually formed of nitride material.

The location feature provides measurements indicating where the defect is relative to the labels (objects in the model). For example, it is important to know whether a defect is on a metal line or in the polyimide area of a PCB. By traversing the defect pixels against the reference Label Image, measurements such as the percentage of defect in a certain area can be obtained.

We provide two measures for location. One is location based on defect boundary information. This measurement is very fast as it uses only information derived from the defect boundary pixels. We count the number of boundary pixels $N_i$ that lie within a region of label type i. For instance, $N_{trench}$ would be the number of pixels lying in trench regions of a patterned wafer. Then the location can be measured in terms of the fraction of total boundary pixels that fall within a given region. For instance, the fraction of a defect lying in a trench is $$\text{location trench} = \frac{N_{trench}}{N_{trench} + N_{nitride}}$$

Figure 10:
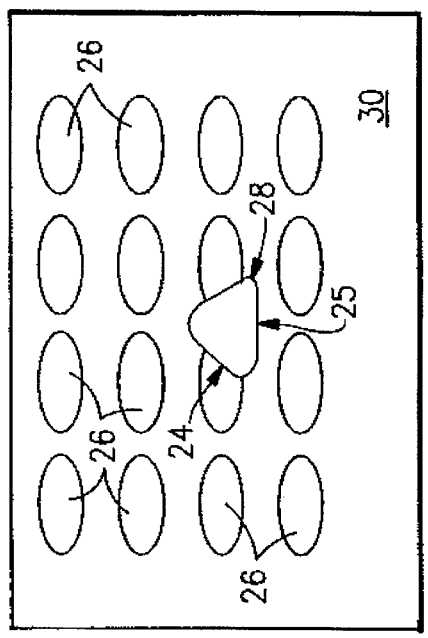
FIG. 10 is a representation of a defect region of a semiconductor wafer having trench and nitride regions utilizing the boundary pixels to determine location.
Figure 11:
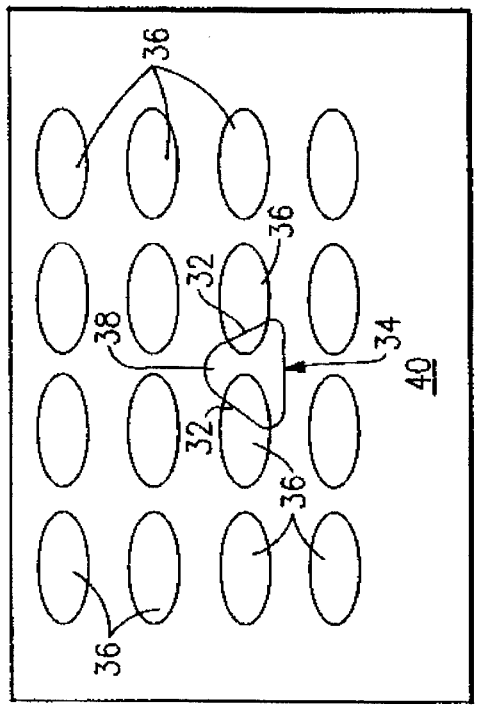
FIG. 11 is a representation of an object scene of a semiconductor wafer having trench and nitride regions showing a defect region and the method of counting all pixels in a defect to a determined location.

FIG. 10 illustrates this. The boundary pixels 24 of the defect 25 falling in the trench region 26 give rise to $N_{trench}$. The boundary pixels 28 on the nitride region 30 give rise to $N_{nitride}$. The other measure is location based on the entire defect area. This is similar to the above except that instead of counting only boundary pixels we count all the pixels of the defect. FIG. 11 illustrates this. The pixel 32 of the defect 34 falling in the trench region 36 give rise to $N_{trench}$. The pixels 38 on the nitride region 40 give rise to $N_{nitride}$.

The color contrast feature measures the contrast between the color of the defect and the color of the area surrounding the defect. This innovation is achieved by comparing the defect color measurements against the Adaptive Distribution for color. For example, we can measure whether a defect is brighter or darker than its surrounding pixels by comparing its brightness measurement against the brightness measurement distributions of the normal pixels. Such measurements provide a direct way of describing/classifying defects in relative and/or linguistic terms such as yellowish, reddish, brighter, etc.

One texture measurement of interest is that of fuzziness. This measurement is useful for deciding whether a defect is out of focus. An out-of-focus object extends beyond the plane under inspection, and is indicative of a foreign material on top of the surface. The fuzziness is computed by measuring the color or brightness gradients across the defect boundary (which is the convex hull) or the interior pixels. From a mathematic viewpoint, we can consider this as the computation of a line integral around a closed contour, $$z = \oint_c f(x)dx$$

where C is the contour along which the integration is performed, and f(x) is the function which is evaluated along the contour.

Frequently there is a need to decide whether a defect is dark or bright, or whether it has a fuzzy cotton ball appearance or not. Texture measures provide these answers. For example, certain kinds of defects, e.g. surface foreign material have a shading around their border. The appearance is similar to that of the fuzzy boundary of a cotton ball. In order to measure this, first the convex hull of the cluster is computed. This defines a contour along which a measurement can be performed. If one wants to measure contrast, the sum of the intensity gradient along the contour is measured. Thus, we measure $$\text{Boundary contrast} = \sum_{\text{convex hull}} \text{intensity gradient}$$

Figure 15:
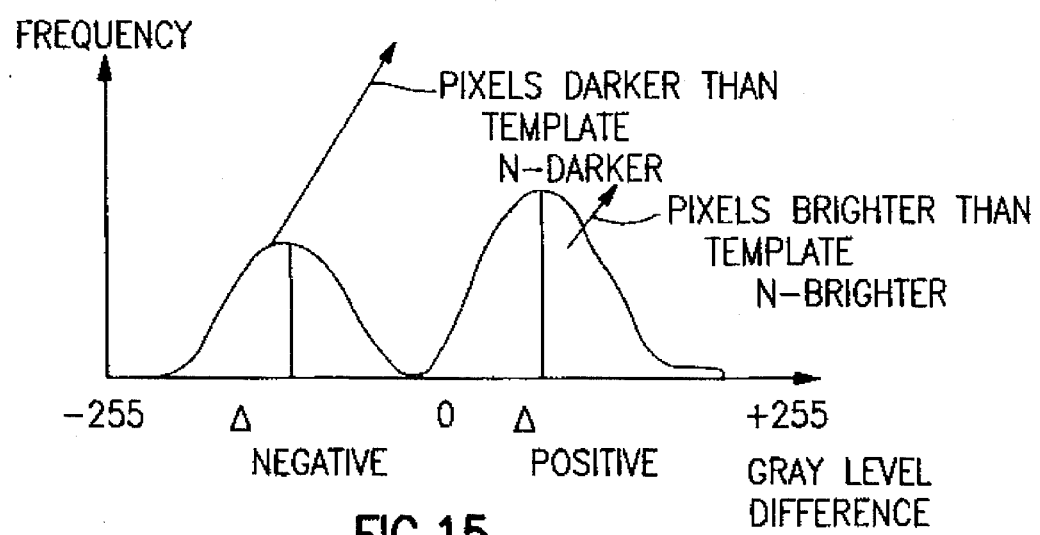
FIG. 15 is a graph showing the distribution of pixels to determine brightness contrast.

This is normalized with respect to the total number of pixels on the convex hull. The standard deviation of contrast values is also measured across the convex hull. If the defect has a fuzzy appearance, the above value will be low. If the defect has sharply defined boundaries, the boundary contrast will be high. This process provides a relative measure that determines what fraction of the defect is brighter than the corresponding region in the template image. The defective region being analyzed will very often be composed of some pixels which are brighter than the template and some which are darker than the template. FIG. 15 shows the distribution of pixels in the difference image (original image minus golden template) corresponding to a defect region. This is called "Interior contrast ratio"

$$\text{Interior contrast ratio} = \frac{N_{brighter}}{N_{brighter} + N_{darker}}$$

There is also provided a quantity "Interior contrast magnitude" which is

Interior contrast magnitude = $\Delta_{positive} - \Delta_{negative}$ where $\Delta_{positive}$ refers to the average intensity in excess of the values specified by the template, and similarly for $\Delta_{negative}$. If the "Interior contrast ratio" is high it means that the defect is bright. If the "Interior contrast magnitude" is high, it indicates that the defect contains both bright and dark regions.

Color measurements include the first and second moments of the red, green, and blue measures. Color measures are also determined by providing the mean rgb values and their standard deviations. Also, useful information on a property called multiple discoloration is also provided. This essentially means that several regions in the defect have different colors. In order to make this judgment, the average color for each region is computed, and if the average colors of at least two regions differ, there is a case of multiple discoloration.

The novel aspect in this computation is the use of a Uniform Color Space to compute the average. The MTM Transform as described in Miyahara and Yoshida, "Mathematical Transform of (R,G,B) color data to Munsell (H,V,C) data," SPIE Vol. 1001, Visual Communications and Image Processing, pp. 650–657, 1988 is used to convert the RGB values into (H,V,C) (hue, value and chroma) coordinates in a uniform color space. The averages are computed in (H,V,C) space instead of (R,G,B) space.

It is also useful to determine if the defect is segmented into regions that fall in different label types—e.g. regions that fall in trench and regions that fall in nitride. This is done by overlaying the reference label image on the detected defect and performing region analysis on the resulting binary image. This segmentation leads to useful measures of relative defect size. For instance, one is able to tell how many trenches the defect covers. This provides another feature to be used in classification—one can have a large trench defect covering several trenches or a small trench defect covering few. This is especially useful because memory products are designed with a certain redundancy, and knowing the size of the segmented defect enables one to determine whether the defect is repairable or not.

Tables 1 through 6 are examples of six different feature measurements for a defect in a patterned semiconductor wafer.

TABLE 1

| FEATURE | DESCRIPTION | MEASUREMENT |
| --- | --- | --- |
| Total Area: | total defect area for this cluster (Euclidean area) | 710.00 |
| Max Area: | area of the maximum defect region within this cluster | 184.50 |
| Avg. area: | total area divided by number of regions in this cluster | 71.00 |
| Hull area: | Area enclosed by the convex hull for this cluster | 2234.50 |
| AREA BASED FEATURES | | |

TABLE 2

| FEATURE | DESCRIPTION | MEASUREMENT |
| --- | --- | --- |
| Location-0: | Fraction of the defect BOUNDARY that lies in the border region | 0.26 |
| Location-1: | Fraction of the defect BOUNDARY that lies in trench | 0.84 |
| Location-2: | Fraction of the defect BOUNDARY that lies in nitride | 0.16 |
| LocationA-0: | Fraction of the defect AREA that lies in the border region | 0.10 |
| LocationA-1: | Fraction of the defect AREA that lies in trench | 0.93 |
| LocationA-2: | Fraction of the defect AREA that lies in nitride | 0.07 |
| Short: | Decides whether a defect shorts two trenches | NO |
| LOCATION BASED FEATURES | | |

TABLE 3

| FEATURE | DESCRIPTION | MEASUREMENT |
| --- | --- | --- |
| Avg. Circ: | Average circularity of a region in the defect cluster | 2.33 |
| Max. Circ: | Maximum circularity among all regions in the defect cluster | 6.36 |
| Hull Peri: | Perimeter of the convex hull that encloses the defect | 188.45 |
| Hull Circ: | Circularity of the convex hull that encloses the defect | 1.26 |
| Hull. Eccen: | (Hull eccentricity), which is ratio of length to width of the defect | 1.73 |
| SHAPE BASED FEATURES | | |

TABLE 4

| FEATURE | DESCRIPTION | MEASUREMENT |
| --- | --- | --- |
| Comp 1 on 2: | Is the fraction of trench | 0.00 |

TABLE 4-continued

| FEATURE | DESCRIPTION | MEASUREMENT |
|---|---|---|
| | pixels occurring in the nitride area | |
| Comp 3 on 2: | Is the fraction of true defect pixels in the nitride area | 0.81 |
| Comp 2 on 1: | Is the fraction of nitride pixels occurring in the trench area | 0.00 |
| Comp 3 on 1: | Is the fraction of true defect pixels in the trench area | 0.72 |
| Comp 1 on 3: | Is the fraction of true defect pixels in the whole defect cluster | 0.76 |// COMPOSITION BASED FEATURES

TABLE 5

| FEATURE | DESCRIPTION | MEASUREMENT |
|---|---|---|
| Mean contrast: | mean contrast around convex hull | 63.69 |
| Std. contrast: | standard deviation of contrast around convex hull | 38.18 |
| I. Cont Ratio: | interior contrast ratio | 0.93 |
| I. Cont Mag: | interior contrast magnitude | 0.12 |
| Lum. contrast: | luminance contrast | 0.36 |// CONTRAST BASED FEATURES

TABLE 6

| FEATURE | DESCRIPTION | MEASUREMENT |
|---|---|---|
| Red: | the average red value | 129.20 |
| Green: | the average green value | 138.39 |
| Blue: | the average blue value | 45.50 |
| Bright: | is the average gray level | 104.36 |
| Std. Red: | refers to the standard deviation of the R values | 28.65 |// COLOR BASED FEATURES Classification of defects presents some problems not encountered in other types of pattern recognition applications. These problems arise from the following observations:

1. The concept of "defect" and of particular categories of defects, is often imprecise.

2. Defects are exceptional events, and occasionally do not conform to standard probability distributions or statistical assumptions.

Fuzzy logic is a mathematical discipline for modeling the vagueness and imprecision typical of human reasoning. In fuzzy logic it is natural to model an imprecise concept such as "gross defect". Furthermore, in contrast to traditional artificial intelligence (AI) systems, fuzzy systems can deal simultaneously with a number of possibly conflicting rules. This is a better model of the way human beings make decisions based on judgement.

A computational architecture for encoding such loosely structured rule bases has been developed using fuzzy logic and is known as fuzzy inference. The details of this architecture are explained in numerous references, such as Zadeh, "Outline of a new approach to the analysis of complex systems and decision processes," IEEE Transactions on Systems, Man and Cybernetics, vol. 3, pp. 28–44.

The present invention is a novel use of fuzzy logic for defect classification. Each rule associates features with a particular class by means of reference sets, or linguistic terms, defined as fuzzy sets on the domains of feature components. For example, we may encode a rule such as "If the area of the defect is large or the number of regions is very large, then the defect is gross". "Area" and "number of regions" are features, "large" and "very large" are reference fuzzy sets defined on the values of these features. A given value for area may be "large" and "very large" are reference fuzzy sets defined on the values of these features. A given value for area may be "large" to a degree which ranges between zero and one.

Rules operate, or fire, in parallel; that is, independently of one another. The input case, or feature vector, is compared to the reference sets of each rule and an overall degree of similarity is determined. This similarity induces a degree of membership in the class indicated in the conclusion of the rule. When all rules have fired, their outputs are combined to yield a net degree of membership of the input case in each class. This can be considered an uncertainty distribution over the set of classes, but it is not necessarily a probability distribution, which has the constraint that the individual uncertainties must sum to one. For example, one rule may fire partially and the rest not at all, yielding a distribution whose sum is less than one. Or, two or more conflicting rules may fire significantly, giving a distribution whose sum is greater than one. Theorists have given other terms to such distributions, such as credibility in the first case and possibility in the second.

In the following discussion, we assume that there are M rules in the fuzzy rule base, and that the kth rule is in the form of an association $(A_{1k}, \ldots A_{Nk} \rightarrow C_k)$ which relates the values of N features $I_1, \ldots, I_N$ to one of a set of classes $C_i$. We also designate by $I_n$ the universe sets, or domains, of the individual features. $\mu_A$ is the notation for the membership function of a fuzzy set A, which is a mapping from some domain such as $I_k$ into [0,1]. We now consider the inference computation for any set of observed feature values $x_1, \ldots, x_N$ of the inputs.

Step One: Convert the $x_i$ into fuzzy sets $X_j$. Note this is not necessary if $x_i$ is already in fuzzy form (e.g., a linguistic variable). There are sophisticated forms of fuzzification which are described in the literature. The trivial fuzzification (most commonly used if $x_j$ is a number) is defined by letting $\mu_x$, ($\mu$) by 1 when $\mu=x_j$; and 0 otherwise.

Step Two: Compute the degree of match for each antecedent. For j=1, ..., N $$M_{jk} = \sup_{u \in I_j} \mu X_j \cap A_{jk}(u)$$

Step Three: Combine degree of match for each antecedent to get net degree of match for each rule k $$M_k = \wedge^N_{j=1} M_{jk}$$

Step Four: Multiply degree of match by weight to get the scale factor for each rule.

$$\alpha_k = \omega_k M_k$$

Step Five: For each rule k, k=1, ..., M, compute the output fuzzy set $C_k$, by operating on $C_k$ with the scale factor:

$$\mu C_k = \alpha_k \wedge \mu C_k$$

This output membership function is then interpreted as an uncertainty distribution on the classes $C_i$. Note that in practice, the consequent term in each rule or association (which in theory could also be a fuzzy set on $C_j$) is a crisp singleton, i.e. a specific class. However, the fuzzy method can still be used when knowledge is not that specific.

Step Six: Merge the output of each rule into the net output fuzzy set C'.

$$\mu C' = V^M{}_{k=1} \mu C_k,$$

There is flexibility here in the form of the V operator, which could be maximum, sum, or any triangular co-norm. The choice should reflect to some extent the degree of independence of the rules. Thus, one should not sum rule outputs unless one knows the rules to be independent. Conversely, choosing the merge operator to be maximum gives a bias to the rule with the strongest degree of match, allowing one rule with a strong output to outweigh several rules with slightly weaker outputs.

Step Seven: Interpret the net uncertainty distribution which is obtained from the previous step. Generally, the user will want to know the one or two classes which yield the best degree of membership, and/or the confidence level associated with the decision to call the input case a member of a specific class C. How one assigns a confidence depends on the degree of exclusion between the classes. If the classes are mutually exclusive and exhaustive, one may extract a confidence level by normalizing the distribution by the sigma count of the distribution. (This turns each degree of membership into a percentage of the total degree of membership.) In the case where one cannot make such assumptions, one can simply associate confidence with the calculated degree of membership.

Figure 16:
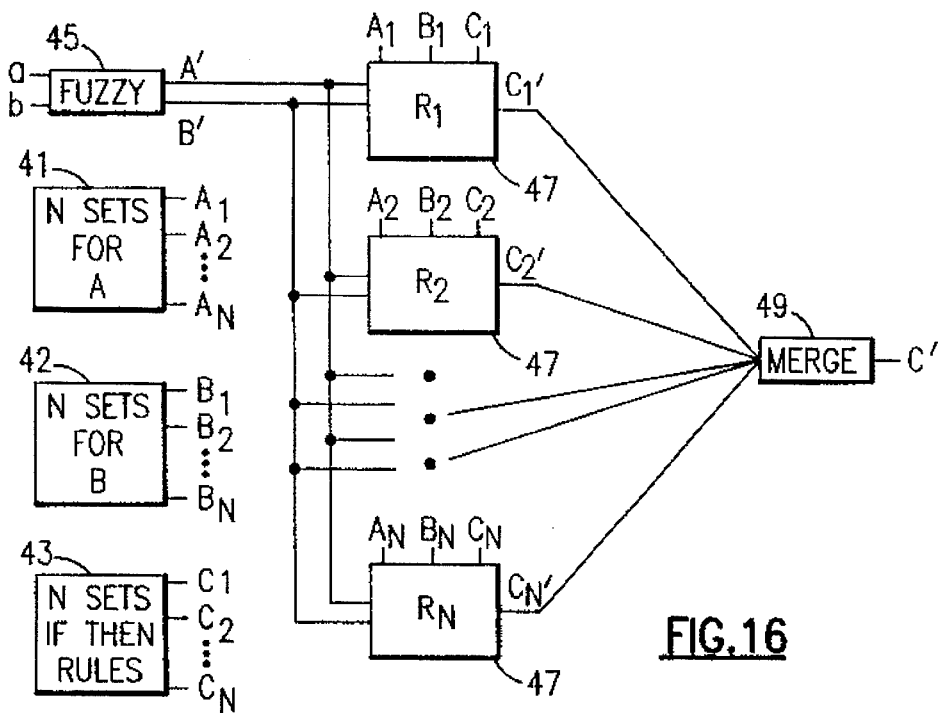
FIG. 16 is a block diagram of a two input fuzzy inference engine.

FIG. 16 provides a block diagram of the fuzzy inference engine for the case of two inputs. In this example, the inference engine includes means 41 for storing N feature fuzzy sets for each of defect feature measurements A and B and means 43 for storing if-then class rules having an output class $C_1 \ldots C_N$ derived from the feature fuzzy sets. Means 45 converts the defect feature measurements into fuzzy logic parameters. Means 47 compares the fuzzy logic parameters with each feature fuzzy set of each class rule to produce a degree of match for each feature fuzzy set for each class rule. Means 47 further combines the degree of match for each fuzzy set of each class rule to produce a degree of match for each class rule. Means 49 combines the degree of match for each class rule to produce a defect class fuzzy set for each object defect.

The description has so far dealt with rules which provide support, or evidence for a particular classification. The fuzzy inference method can also factor in the contribution of rules which provide refutation, or evidence against a particular classification. We may use, respectively, the two terms supportive and exclusionary rules. When both types of rules are present in a rule base, two uncertainty distributions are built: one associated with credibility (presence of supporting evidence) and another with possibility (absence of refuting evidence). These two distributions must be reconciled before asserting a confidence level for any choice of classification. A general method for reconciling two such distributions derives from Dempster's rule of evidence combination which is known to those in the art.

For example, suppose P is the supportive (positive) rule base and N is the exclusionary (negative) rule base. After evaluating each rule base according to the method just described; we obtain two fuzzy set outputs with membership functions $\mu_P$ and $\mu_N$ respectively. To reconcile these two distributions we apply the following method:

Step One: convert $\mu_P$ to a credibility measure. A credibility measure must be bounded from above by a probability measure (something cannot be more credible than it is probable). Thus, if the sum of memberships $\Sigma_x \mu_P(x)$ is less than or equal to 1 there is nothing more to do, otherwise we divide each membership value $\mu_P(x)$ by the sum of memberships.

Step Two: Convert $\mu_N$ to a possibility measure. A possibility measure must be bounded from below by a probability measure (something cannot be more probable than it is possible). To do this, we first convert $\mu_N$ to a credibility measure as in the previous step, then replace each membership $\mu_N(x)$ by its reciprocal $1-\mu_N(x)$. It is evident that after doing this replacement the sum of memberships $\Sigma_x \mu_N(x)$ will be greater than or equal to 1, as desired.

Step Three: Merge the two distributions $\mu_P$ and $\mu_N$ into a single distribution $\mu_{PN}$ using the method described in Possibility Theory by Dubois and Prade, pp. 138–140:

$$\mu_{PN}(x) = \max(0, \mu_N(x) + \mu_P(x) - 1)/(1 - \min(\mu_P(x), 1-\mu_N(x)))$$

if using max-min inference, or $$\mu_{PN}(x) = \mu_P(x)\mu_N(x)/(1-\mu_P(x)(1-\mu_N(x)))$$

if using sum-product inference.

Figure 17:
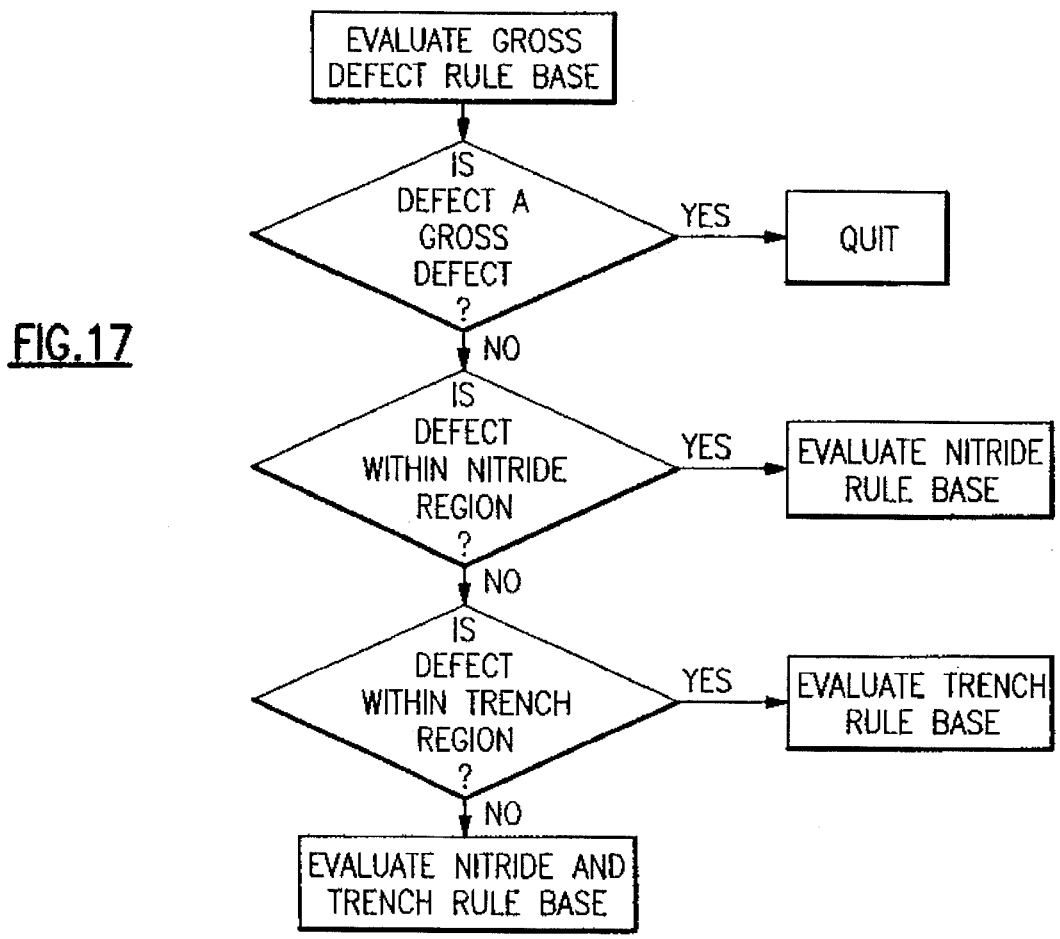
FIG. 17 is a flow chart of the fuzzy inference engine utilizing a hierarchial decision process.

Any realistic approximation to human reasoning processes in classification applications will not use a single fuzzy rule base, since this does not effectively model that portion of the decision process which is hierarchical. Also, a single rule base requires all inputs to be present before the computation can be completed, since all rules must be evaluated. This can result in the calculation of numerous features which are simply discarded, since the rules that use them may not apply. In real-time or high-throughput applications this wasted computational effort can be serious. Therefore, the recommended approach is to apply a partial "divide and conquer" strategy by creating small rule bases which apply to certain subsets of the overall problem. In wafer defect classification, separate rule bases may deal with different areas of the wafer. An example of this is illustrated in FIG. 17. The hierarchical procedure described here first tries to determine if the defect can be classified as "gross". If not, it invokes different rule bases depending on whether the defect lies within the trench region of the wafer, lies within the nitride region, or straddles both regions. Hierarchical decisions can be implemented by evaluating the results of previous fuzzy inference steps or by making crisp decisions based on key feature values. In our methodology, we provide this capability by means of a procedural language which allows the high-level control flow of the classification process to be expressed. Conditional expressions involving both fuzzy operations (computations involving degrees of membership or confidence levels) and traditional arithmetic and logical operations are allowed. Execution of various fuzzy inference steps then depends on the results of this expression evaluation.

The present invention has been implemented as an automated optical defect classification (ADC) system. The system consists of two environments: The user-friendly XWindow-based development environment allows a user with basic knowledge in machine vision to interactively develop, test, and update solutions for a particular product. The production environment provides an interface to work with various operating environments. The user provides the hooks between ADC and the defect review stations through the production interface. A customized solution consists of configuration files, reference images, and a defect definition file (fuzzy rulebases). These files are generated by using the development environment and used as the input arguments to the production environment. One beauty of the system is its usability: custom solutions can be developed with the friendly, interactive graphical user interface. The solution thus developed can be directly fed into the production environment without having to modify the program.

The development environment provides a list of pull-down menus and display panels for images, parameters, feature values, classification results, etc. It allows the user to step through each processing stage and adjust the parameters or rules as appropriate.

One embodiment of the invention includes an improvement in the input to golden image alignment procedure: it aligns the images by aligning the golden image corners to the corresponding input image corners. An alignment is found when a corner satisfactorily aligns, with a high correlation coefficient, with its corresponding corner in the input image. The idea is to align a golden image corner with a defect-free corner in the input image, thus the effect of the defect location on the alignment accuracy is minimized.

The description of the fuzzy inference language used for the defect definition is provided below. In short, the user can use linguistic terms such as "small", "medium" and "large" to describe defect measurements through trapezoidal or piece-wise linear fuzzy membership functions. Defect classes can be defined as the possible values of the defect fuzzy variable. The value of defect is defined by symbolic inference rules in terms of the fuzzy, linguistic descriptions of the defect measurements. The rules can be grouped into rulebases, each tailored to classify defects in a particular situation, to gain processing efficiency and accuracy. The control of rulebase evaluations can be specified in a high-level, procedural language that supports rulebase evaluation, conditional branches on the results of a rulebase evaluation, and loops. With a built-in defect definition rule-base editor, the user can edit the membership functions, rules, and classification procedures using the built-in editor and test the changes by simply applying them to input cases. There is no compile or linking step required to apply the changes, and the user never leaves the application development environment.

At run-time, the fuzzy rule evaluation requests features from the image analysis module by name. Thus, the image analysis module does not have to present the feature data to the inference procedure according to any fixed format, nor does it have to precompute features which may or may not be used. New features can be introduced to the inference process simply by defining them in the fuzzy procedural language.

The following is a description of the input language for programming fuzzy inference for one implementation of the defect classification system of the present invention. Fuzzy rules are basically if-then statements dealing with the values of certain variables. How you think of these variables depends on the application; for example, in automatic defect classification a variable is typically an image feature. Variables may belong to variable classes. If a group of variables share the same representation, it may be convenient to define a variable class for them. For example, the variable class color intensity may be defined, with the particular variables, red, green and blue later defined as instances of that class. The object of this is that fuzzy set definitions based on the variable class can be shared by all instances of that class.

These are either continuous or discrete. Continuous variables have values distributed over a specified range of real numbers. Discrete variables may take only a small, finite set of values, which may or may not be numerical. For example, the variable defect class may take values FM, WT, CI, etc.

Each variable or variable class you define has a name which you give it. Thus, to define a variable class you provide:
1. A name.
2. Whether it is continuous or discrete.
3. If continuous, the minimum value and maximum value (i.e. the range).
4. If discrete, the number of discrete values, or a list of symbolic values (e.g. the defect classes above).

The following are examples:
 var_class PERCENTAGE continuous 0.0 to 100.0
 var_class PERCENTAGE continuous [0,100]
 var_class DEFECT_CLASS discrete WT,FM,GD,CI
 variable RED of COLOR_INTENSITY var_class, variable, continuous, discrete, to, and of are all keywords of the input language. Note that keywords are lower-case only, as in C. A string matches a keyword if it matches in the first 8 characters. Underscores in keywords may be omitted; thus "var_class" and "varclass" are equivalent. A good convention is to use lower case only for keywords, and make all user-defined names upper case.

A variable can be defined as an instance of a variable class, or it can be defined in the same way as a variable class (except using the keyword variable instead of var_class), in which case it defines its own unique variable class with the same name. Names of variables must all be distinct, and names of variable classes must all be distinct.

Fuzzy sets are defined as linguistic terms relating to the values of certain variables or variable classes. To define a fuzzy set, you must provide:
1. A name;
2. The variable or variable class the fuzzy set relates to;
3. The membership function, which may be
 (a) Normalized trapezoidal (four point form),
 (b) Fit (fuzzy bit) vector (discrete membership values),
 (c) Segmented (piecewise; set of points joined by line segments).

The fit vector membership functions can only be used for discrete variables or variable classes.

When defining a fuzzy set piecewise (with the segments keyword) you provide a list of points: each point is a value of the variable followed by the degree of membership at that value. The first and last points must have zero degree of membership, and the points must be in increasing order of the first coordinate (i.e. the value). If a "step" is required in the membership function, you supply two points for the coordinate where the step occurs; the point with lesser degree of membership represents the limit of membership degrees as the values approach the coordinate from below (for a rising step) or above (for a descending step). The point with greater degree of membership is the actual degree of membership at the value where the step occurs. Thus, for example, the crisp set of numbers between 0 and 2 inclusive (which has steps at 0 and 2) can be represented piecewise as (0,0), (0,1), (2,1), (2,0).

The following are examples:
fuzzy_set HIGH of PERCENTAGE trapezoidal (70.0, 90.0, 100.0, 100.0)
fuzzyset F of X vector (0.0, 0.2, 0.5, 1.0, 0.3, 0.0)
fuzzyset G of Y segments (0,0), (1,0.3), (2,1), (3,0.7), (4,0)

In this example, fuzzy_set, vector, trapezoidal, segments are keywords. Fuzzy set names must be unique only within the variable or variable_class. Thus, you can define a fuzzy set "high" for intensity and another fuzzy set "high" for percentage, if you want.

The point of all this definition of things is eventually to create a fuzzy rule base. To do this, you must provide: (1) a name; (2) Computational options (if different from the default); (3) A list of rules. The rules are in the general form "If X is A and Y is B and . . . then Z is C". There may be a number of antecedents but only a single consequent (for the initial implementation, multiple consequents may be supported later). X, Y, Z are variables, and A, B, C are fuzzy sets defined on the respective variables. (A, B, C may also be symbolic values of a discrete variable, in which case they are treated as singleton sets where the membership value is 1 at the stated value and 0 elsewhere.) The consequents of all rules in a rule base must deal with the same variable. Antecedents will in general deal with the same variables, but not all antecedent variables need have their own clause in each rule. Ordering of variables in antecedent clauses need not be identical for all rules in a rule base. The software will put things in the proper order internally.

A rule base is exercised by supplying it with a value for each of the antecedent variables which appear in at least one rule. Thus, the input to a rule base is a vector of input values (e.g. a feature vector for defect classification applications). Input values for continuous variables are real numbers, for discrete variables, the symbolic value, or an integer which is the index into the discrete set. Input values can also be in the form of fuzzy sets.

Each "if then" rule of the rule base defines a fuzzy and-gate. The membership values of the inputs in their corresponding antecedent fuzzy sets are "and-ed" together and this result is used to scale the fuzzy set of the consequent clause. This scaled fuzzy set is the output of the and-gate.

The output of each rule then goes into a fuzzy or-gate. Here the fuzzy set outputs are "or-ed" together to construct the output of the entire rule base for this instance of inputs. This output can be left fuzzy or it can be defuzzified, that is, translated into a real number or discrete set member.

There are various computational options which can be specified. These relate to and-gate operation, or-gate (merge) operation, and defuzzification. The and-gate operation can be specified as min or product (default if not specified is min). min is geared more toward logical operations such as in a classifier; product sometimes works out better for function estimation or real-time process control. The or-gate operation can be specified as max, or sum. (Default is max) Again, which you choose depends on the application. If the or-gate is specified as sum an additional normalization step is required if the output is to be left fuzzy. Defuzzification can be specified as max or centroid. (Default is centroid.) Centroid is usually desired if the output variable is continuous, max is more common if the output variable is discrete. Remember also that the centroid is uniquely defined for any fuzzy set, although it may not represent optimal membership. The maximum membership is optimal but not necessarily unique.

An example for specifying a fuzzy rule base is as follows:

```
rule_base RB1 (and_gate=product,
               or_gate=weighted_sum,
               defuzzification=centroid)
begin
    if X1 is A and Y1 is B then Z is C     weight 0.8
    if X1 is D and Y2 is E then Z is F     weight 1.0
    ... <more rules>
end
```

Weights are only required if sum is specified for the or-gate. The fuzzy set outputs of each and-gate are further scaled by the rule weights before being summed in the or-gate. Weights must be between 0.0 and 1.0 inclusive. If a weight is not given explicitly for a rule, the weight is 1.0 default.

Another option is to have both positive ("If X is A then Y is B") and negative ("If X is A then NOT Y is B") rules in rule base. This is effective only if the consequent variable is discrete and the output is left fuzzy. For each element in the domain of the consequent variable, the positive and negative rules contribute a measure of belief (or credibility) and a measure of disbelief (or possibility). As the inference procedure progresses, these two uncertainty distributions are built. At the end, they are resolved into a single distribution using Dempster's rule with either max-min (if the or gate is max) or sum-product (if the or gate is sum). The negative rules option must be specified in the options list with the keyword neg_rules. A negative rule is then indicated by the keyword not appearing after then and before the consequent clause, e.g. if X is A then not Y is B.

Procedures are now included to provide flow of control. A procedure is a list of statements bracketed by the beginend keywords. Procedures have names. Individual statements in the procedure are terminated by semicolons, as in C. (The semicolon is a terminator, as in C, not a separator as in Pascal. Thus the statement before the end must also terminate with a semicolon.)

A statement is either a declaration of a local variable or a computational action to be performed. Declarations of local variables are identical to declarations of global variables, except that they are only accessible from within the procedure. They can be used to store temporary results.

The reset statement is simply the keyword reset. It sets values of all global variables to <undefined>. This will cause a new value to be fetched from the application interface whenever the value of a variable is used. For instance, if you wanted to start classification of a new image, you would begin a procedure with reset. (Local variables of a procedure are always reset on entry to the procedure.)

The eval and eval_trace statements invoke fuzzy rule bases. They are formed by concatenating the name of the rule base, a period, and the keywords eval or eval_trace. (E.G. DT1.eval_trace). Both keywords invoke the rule base. The eval_trace form saves information in the trace buffer for debugging. You may then display this information on standard output by a statement such as DT1.print_trace. You must give the name of the rule base to the print_trace statement because the rules contributing to the output are printed out in if-then form, which is obtained from the rule base and is not stored in the trace buffer.

The print statement can be used to display things on standard output, again mostly for debugging purposes. The form of the statement is the keyword print followed by a comma-separated list of expressions to be printed. Each expression is printed according to a standard style, depending on the type of the result. A simple example is print "defect is" DEFECT, "\n" or print "possibility of gross defect is", DEFECT is GR, "\n"

The assignment statement is used to set the values of variables. This is just a statement with the general form <variable>=<expression>. The expression is evaluated and the result assigned to the variable. Note that the result of rule base evaluation will be assignment to a consequent variable, so no special statement is needed to accomplish that.

The If-then statement is just like the if statement in C except that (1) you don't need a parenthesis around the conditional part, and (2) the then keyword marks the end of the conditional part. For example, in C you might say if(cond) s1; else s2; but in this form of the if statement you would say if cond then s1; else s2. The condition is any statement that evaluates to something numeric. In particular, this includes membership evaluation like "AREA is BIG". Any non-zero result causes the condition to be considered true. You can use fuzzy truth values by comparing them; e.g. "if(DEFECT is GR)>0.9 then . . . " etc.

The Do and while statements are also similar to the C statements. The forms do <statement> while <condition> and while <condition> do <statement>. The difference of course is that in the first form the statement is always executed at least once.

The return statement causes execution of a procedure to terminate and return the result of evaluating the expression following the return keyword. This result is captured in a varvalue structure which can be examined by the application program.

A compound statement is an aggregated list of statements. This is primarily useful in if or do-while constructs. The list of statements is preceded with begin and terminated by end. As always, individual statements in the list are terminated by semicolons.

The invention can be applied to many inspection applications that require not only counting but also analyzing the defects. The system of the invention can be used for the many inspection applications in the electronic manufacturing industry, such as PCB inspection, MLC (for EF) inspection, and semi-conductor inspection.

Since the classification system is modular, portions of it can be used for any image-related classification task. For instance, if a region-of-interest is specified by a user or prior-level system, then the system can classify this region based on the built-in features and user defined rules. This observation enables the system to be used in a wide range of classification tasks, some of which are listed below.

1. Biomedical applications: An expert can circle the region-of-interest in a medical image, and the system can classify this region based on quantitative measurements which are difficult for the expert to perform.

2. Lumber Inspection: Defective areas in wood can be detected through processes like thresholding or segmentation. These defective areas can then be classified by the system.

3. Inspection of agricultural products.

4. Print quality assessment and inspection.

While the invention has been particularly shown and described with respect to preferred embodiments thereof, it would be understood by those skilled in the art that the foregoing of the changes in form and details may be made therein without departing from the spirit and scope of the invention which should be limited only by the scope of the appended claims.

Having thus described the invention, what is claimed as new and what is desired to be secured by Letters Patent is:

1. A digital computer for automatically classifying defects in an object comprising:

means for forming a defect image from a digital input image of an object;

means for forming an adaptively labeled defect image from said digital input image and a reference label image of aid object;

means for creating a plurality of defect feature measurements of a defect from at least said defect image, and said adaptively labeled image;

fuzzy logic inference engine means having a plurality of if-then defect class rules each based on a plurality of fuzzy sets of fuzzy logic parameters, means for converting said defect feature measurements into fuzzy logic parameters and applying said converted parameters to said if-then rules to compute a delete class fuzzy set for each defect; and means lot deriving output data from each said defect class fuzzy set which classifies each defect.

2. The system of claim 1 further including means for forming said digital input image from an optical image of said object.

3. The system of claim 1 wherein said defect detecting means includes means for aligning and comparing said digital input image with a digital reference image to produce a binary defect image where ones correspond to defect pixels and all other pixels are set to zero.

4. The system of claim 3 wherein said defect detecting means includes means for labelling each pixel of said binary defect image with a label that identifies which element of said object is represented by said pixel.

5. The system of claim 4 wherein said labelling means comprises means for labelling each non-defect pixel with the same label for that pixel in a labelled digital reference image and means for adaptively labelling said defect pixels.

6. The system of claim 5 wherein said adaptive labelling means comprises means for forming a label distribution of each type of label of non-defect pixels in the vicinity of the location of defect pixel from said labelled digital reference image, means for measuring a distribution similarity parameter of said defect pixel and means for comparing the measurement of said distribution similarity parameter and said label distributions for each type of label to produce a similarity result and means for labelling said defect pixel based on said similarity result.

7. The system of claim 6 wherein said adaptive labelling means includes means for adaptively forming said labelled digital reference image.

8. The system of claim 4 wherein said feature measurement means includes means for grouping connected defect pixels into defect regions.

9. The system of claim 8 wherein said feature measurement means include means for grouping said defect region into defect clusters based on one or more region grouping criteria.

10. The system of claim 9 wherein said feature measurement means includes means for measuring and storing defect region feature measurement data.

11. The system of claim 10 wherein defect region measurement means includes means for measuring one or more of location, area, perimeter and shape of the defect regions.

12. The system of claim 11 wherein said region grouping criteria are based on said defect region feature measurement data.

13. The system of claim 12 wherein said defect regions are grouped into defect clusters based on the spatial proximity within said labelled binary defect image.

14. The system of claim 9 wherein said defect region grouping means includes means for using a union-find algorithm to compare similarities of the defect regions based on the grouping criteria.

15. The system of claim 10 wherein said feature measurement means includes means for measuring and storing defect cluster feature measurement data.

16. The system of claim 15 wherein said defect cluster feature measurement means includes means for combining the defect region feature measurement data for all defect regions within a defect cluster.

17. The system of claim 15 wherein said defect cluster feature measurement means includes means for calculating a bounding curve for all defect regions within a defect cluster measuring feature measurement data of the bounding curve.

18. The system of claim 15 wherein said defect cluster feature measurement means includes means for measuring one or more of size, shape, texture, location, composition, color and contrast of the defect cluster.

19. The system of claim 1 wherein said fuzzy logic inference engine means comprises:

means for storing one or more feature fuzzy sets for each of said plurality of defect feature measurements;

means for storing said plurality of if-then class rules, said rules having an output class derived from said one or more feature fuzzy sets;

means for converting said defect feature measurements into fuzzy logic parameters;

means for comparing said fuzzy logic parameters with each feature fuzzy set of each class rule to produce a degree of match for each feature fuzzy set for each class rule;

means for combining the degree of match for each fuzzy set of each class rule to produce a degree of match for each class rule;

means for combining the degree of match for each class rule to produce a defect class fuzzy set for each object defect.

20. The system of claim 19 wherein said fuzzy logic inference engine means further includes means for multiplying said degree of match for each class rule by a weighing factor to produce a scale factor for each class rule.

21. The system of claim 20 wherein said fuzzy logic inference engine means further includes means for combining the scale factor with the output class for each rule to produce an output class fuzzy set for each rule.

22. The system of claim 21 further including means for defuzzifying said defect class fuzzy set to classify the object defect as one of a plurality of defect classes.

23. The system of claim 19 wherein said plurality of if-then class rules includes supportive and exclusionary rules.

24. The system of claim 19 wherein said fuzzy logic inference engine means includes control means for producing class outputs for a subset of if-then rules based on one or more conditional expressions and means for producing said defect class fuzzy set based on the subset of class outputs.

25. The system of claim 24 wherein said conditional expressions include fuzzy operations, arithmetic operations and/or logical operations.

26. A method for automatically classifying defects in an object comprising the steps of:

forming a defect image from a digital input image of the object;

forming an adaptively labeled defect image from said digital input image and a reference label image;

creating a plurality of defect feature measurements of a defect from at least said defect image, and said adaptively labeled image;

converting said defect feature measurements into fuzzy logic parameters;

applying said converted parameters to a plurality of if-then rules each based on a plurality of fuzzy sets of fuzzy logic parameters;

computing a defect class fuzzy set for each defect; and deriving output data from each of said defect class fuzzy sets for classifying each defect.

27. The method of claim 26 including the step of forming said digital input image from an optical image of said object.

28. The method of claim 26 wherein said defect detecting step includes aligning and comparing said digital input image with a digital reference image to produce a binary defect image where ones correspond to defect pixels and all other pixels are set to zero.

29. The method of claim 28 wherein said defect detecting step includes labelling each pixel of said binary defect image with a label that identifies which element of said object is represented by said pixel.

30. The method of claim 29 wherein said labelling step comprises labelling each non-defect pixel with the same label for that pixel in a labelled digital reference image and adaptively labelling said defect pixels.

31. The method of claim 30 wherein said adaptive labelling step comprises forming a label distribution of each type of label of non-defect pixels in the vicinity of the location of the defect pixel from said labelled digital reference image, measuring a distribution similarity parameter of said defect pixel, comparing the measurement of said distribution similarity parameter and said label distributions for each type of label to produce a similarity result, and labelling said defect pixel based on said similarity result.

32. The method of claim 31 wherein said adaptive labelling step includes adaptively forming said labelled digital reference image.

33. The method of claim 29 wherein said feature measurement step includes grouping connected defect pixels into defect regions.

34. The method of claim 33 wherein said feature measurement step includes grouping said defect region into defect clusters based on one or more region grouping criteria.

35. The method of claim 34 wherein said feature measurement step includes measuring and storing defect region feature measurement data.

36. The method of claim 35 wherein defect region measurement step includes measuring one or more of location, area, perimeter and shape of the defect regions.

37. The method of claim 36 wherein said region grouping criteria are based on said defect region feature measurement data.

38. The method of claim 37 wherein said defect regions are grouped into defect clusters based on the spatial proximity within said labelled binary defect image.

39. The method of claim 34 wherein said defect cluster grouping step includes using a union-find algorithm to compare similarities of the defect regions based on the grouping criteria.

40. The method of claim 35 wherein said feature measurement step includes measuring and storing defect cluster feature measurement data.

41. The method of claim 40 wherein said defect cluster feature measurement step includes combining the defect region feature measurement data for all defect regions within a defect cluster.

42. The method of claim 40 wherein said defect cluster feature measurement step includes calculating a bounding curve for all defect regions within a defect cluster and measuring feature measurement data of the bounding curve.

43. The method of claim 40 wherein said defect cluster feature measurement step includes measuring one or more of size, shape, texture, location, composition, color and contrast features of the defect cluster.

44. The method of claim 26 wherein said classifying step comprises:

storing one or more feature fuzzy sets for each of said plurality of defect feature measurements;

storing said plurality of if-then class rules, said rules having an output class derived from said one or more feature fuzzy sets;

converting said defect feature measurements into fuzzy logic parameters;

comparing said fuzzy logic parameters with each feature fuzzy set of each class rule to produce a degree of match for each feature fuzzy set for each class rule;

combining the degree of match for each fuzzy set of each class rule to produce a degree of match for each class rule; and combining the degree of match for each class rule to produce a defect class fuzzy set for each object defect.

45. The method of claim 44 wherein said classifying step further includes multiplying said degree of match for each class rule by a weighing factor to produce a scale factor for each class rule.

46. The method of claim 45 wherein said classifying step further includes combining the scale factor with the output class for each rule to produce an output class fuzzy set for each rule.

47. The method of claim 43 further including the step of defuzzifying said defect class fuzzy set to classify the object defect as one of a plurality of defect classes.

48. The method of claim 44 wherein said plurality of if-then class rules includes supportive and exclusionary rules.

49. The method of claim 44 wherein said classifying step includes producing class outputs for a subset of if-then rules based on one or more conditional expressions and producing said defect class fuzzy sets based on the subset of class outputs.

50. The method of claim 49 wherein said conditional expressions include fuzzy operations, arithmetic operations and/or logical operations.

51. The digital computer of claim 1 wherein said plurality of defect feature measurements are created from said defect image, said adaptively labeled image and said reference label image.

52. The method of claim 26 wherein said plurality defect feature measurements are created from said defect image, said adaptively labeled image and said reference label image.

* * * * *

UNITED STATES PATENT AND TRADEMARK OFFICE
CERTIFICATE OF CORRECTION

PATENT NO. : 5,544,256

DATED : August 6, 1996

INVENTOR(S) : Virginia Howard Brecher, et al.

It is certified that error appears in the above-identified patent and that said Letters Patent are hereby corrected as shown below:

Column 1, line 16: "Whale" should read --While--
Column 9, line 9: "$(I_j, Ik)$" should read --$(I_j, I_k)$--
Column 9, line 41: after "image" insert --66--
Column 9, line 42: after "image" delete --66--
Column 10, line 27: after "This" delete -- - --
Column 11, line 66: "$N_2$" should read --$N_1$--
Column 17, line 4: "$V^m k = 1\mu C$ ," should read --$V_k^M = 1\mu C$ --
Column 23, line 51, Claim 1: "aid" should read --said--
Column 23, line 61, Claim 1: "delete" should read --defect--
Column 23, line 63, Claim 1: "lot" should read --for--
Column 24, line 31, Claim 9: "region" should read --regions--
Column 28, line 14, Claim 52: after "plurality" insert --of--

Signed and Sealed this

Twenty-second Day of April, 1997

BRUCE LEHMAN

*Commissioner of Patents and Trademarks*

*Attest:*

*Attesting Officer*